United States Patent
Yarger et al.

(10) Patent No.: US 9,636,348 B2
(45) Date of Patent: *May 2, 2017

(54) 6-SUBSTITUTED ESTRADIOL DERIVATIVES FOR USE IN REMYELINATION OF NERVE AXONS

(71) Applicant: Endece LLC, Mequon, WI (US)

(72) Inventors: James G. Yarger, Cedarburg, WI (US); Steven H. Nye, Mequon, WI (US)

(73) Assignee: Endece LLC, Mequon, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/179,349

(22) Filed: Jun. 10, 2016

(65) Prior Publication Data

US 2016/0279144 A1 Sep. 29, 2016

Related U.S. Application Data

(63) Continuation of application No. 13/426,364, filed on Mar. 21, 2012, now Pat. No. 9,364,486.

(60) Provisional application No. 61/454,873, filed on Mar. 21, 2011.

(51) Int. Cl.

| A61K 31/568 | (2006.01) |
|---|---|
| A61K 31/5685 | (2006.01) |
| A61K 31/565 | (2006.01) |
| A61K 31/57 | (2006.01) |
| A61K 31/566 | (2006.01) |
| A61K 45/06 | (2006.01) |

(52) U.S. Cl.
CPC .......... *A61K 31/565* (2013.01); *A61K 31/566* (2013.01); *A61K 31/568* (2013.01); *A61K 31/5685* (2013.01); *A61K 45/06* (2013.01)

(58) Field of Classification Search
CPC ....... A61K 31/56; A61K 31/57; A61K 31/565
USPC ........................................ 514/171, 178, 182
See application file for complete search history.

(56) References Cited

U.S. PATENT DOCUMENTS

| 4,136,160 | A * | 1/1979 | Cohen ................ G01N 33/6896 206/569 |
|---|---|---|---|
| 9,364,486 | B2 * | 6/2016 | Yarger ................. A61K 31/565 |
| 2010/0130463 | A1 | 5/2010 | Yarger |
| 2012/0071455 | A1 | 3/2012 | Yarger et al. |

FOREIGN PATENT DOCUMENTS

| JP | 1989193529 A | 4/1989 |
|---|---|---|
| JP | 2009510125 A | 3/2009 |
| JP | 2010511625 A | 4/2010 |
| WO | WO2008/067450 A2 * | 6/2008 |
| WO | 2008067450 A2 | 7/2008 |
| WO | 2009149176 A1 | 12/2009 |

OTHER PUBLICATIONS

Vippagunta et al. (Advanced Drug Delivery Reviews, 48 (2001), pp. 3-26.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta et al., "Crystalline Solids", Advanced Drug Delivery Reviews, 48 (2001 ), 3-26.
Souillac et al., "Characterization of Delivery Systems, Differential Scanning Calorimetry", pp. 217-218 (in Encyclopedia of Controlled Drug Delivery, 1999, John Wiley & Sons, pp. 212-227).
Carswell et al., "Neuroprotection by a selective estrogen receptor Beta agonist in a mouse model of global ischemia", Am J Physiol Heart Circ Physiol, 2010, vol. 287, 1501-04.
Crawford et al., "Oestrogen receptor Beta ligand: a novel treatment to enhance endogenous function remyelination", Brain, A Journal of Neuroloy, 2010, val. 133, 2999-3016.
Donzelli et al. "Neuroprotective Effects of Genistein in Mongolian Gerbils: Estrogen Receptio-Beta Involvement", Pharmacal. Sci., 2010, vol. 114, 158-167.
Schumacher et al., "Progesterone and progestins: neuroprotection and myelin repair", Current Opinion in Pharmacology, 2008, 8, 740-746.

* cited by examiner

*Primary Examiner* — Jennifer M Kim
(74) *Attorney, Agent, or Firm* — Reinhart Boerner Van Deuren s.c.

(57) ABSTRACT

Disclosed is a method of remyelinating axons with 6-substituted estradiol compounds of the formula

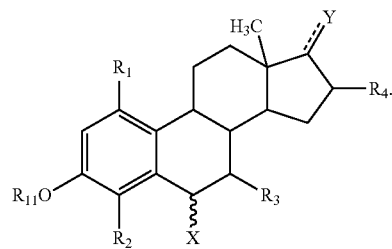

The methods can be used to treat a variety of demyelinating diseases.

14 Claims, 6 Drawing Sheets a)

FIG 2 - Cont.
b)
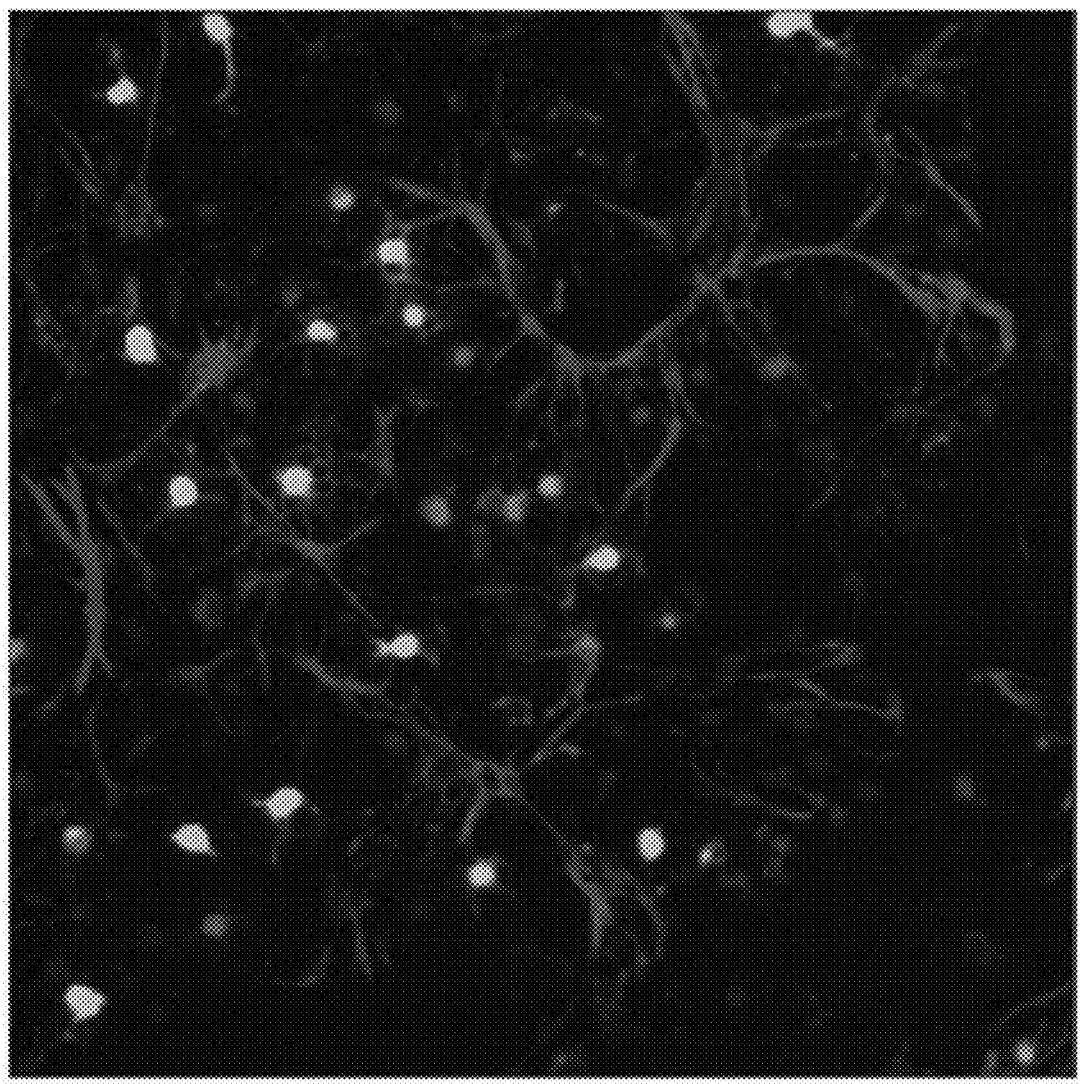

FIG 2 - Cont.
c)
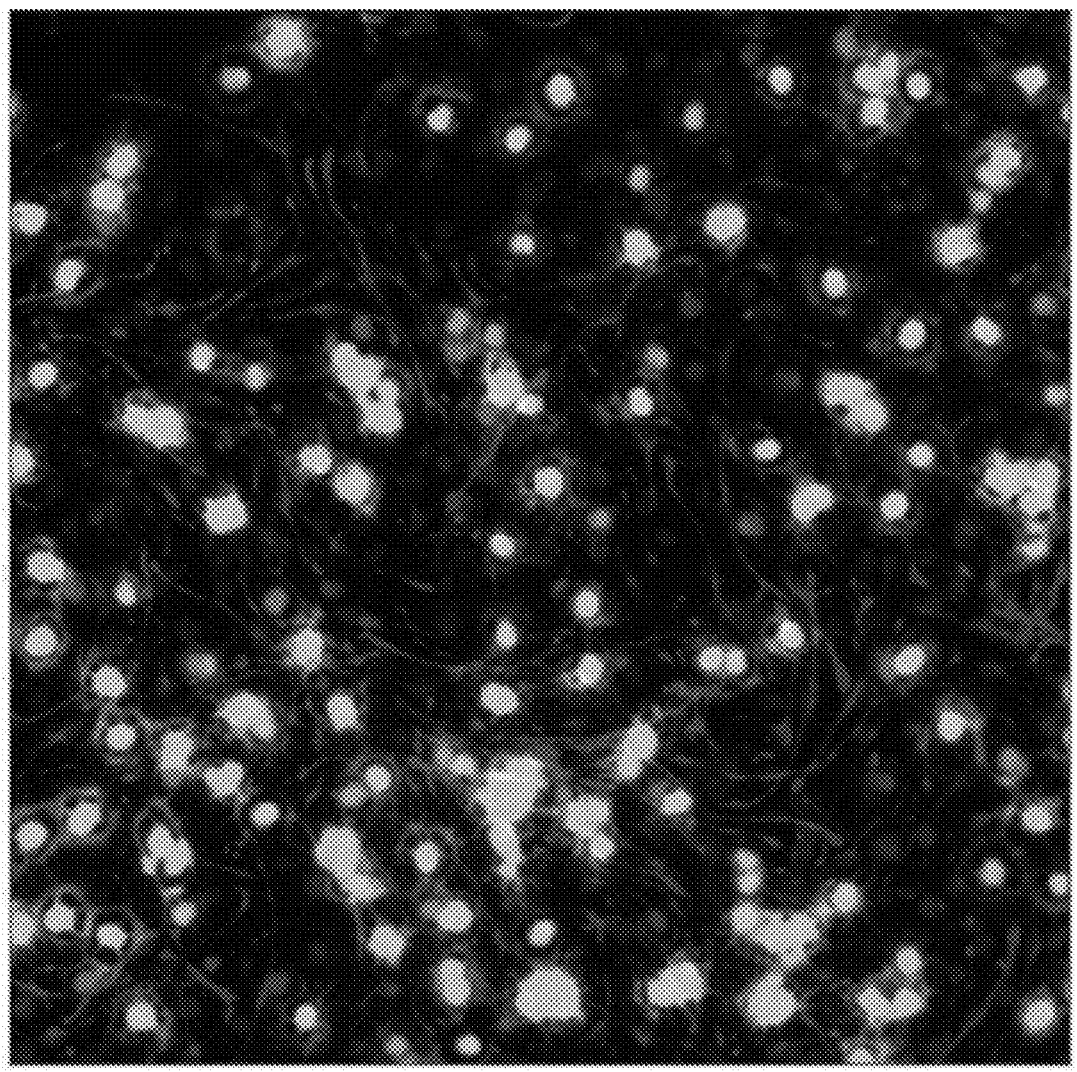

6-SUBSTITUTED ESTRADIOL DERIVATIVES FOR USE IN REMYELINATION OF NERVE AXONS

This application claims priority to and the benefit of application Ser. No. 13/426,364 filed Mar. 21, 2012 and issued as U.S. Pat. No. 9,364,486 on Jun. 14, 2016, which claimed priority to and the benefit of provisional application Ser. No. 61/454,873 filed on Mar. 21, 2011, each of which is incorporated herein by reference in its entirety.

FIELD OF THE INVENTION

The present invention relates to a method of remyelinating axons with 6-substituted estradiol compounds and their pharmaceutically acceptable salts or prodrugs. The method is useful in the treatment of demyelinating diseases, such as multiple sclerosis.

BACKGROUND OF THE INVENTION

Myelin is an electrically insulating material which encases the axons of neurons forming a layer known as the myelin sheath. The primary purpose of myelin is to increase the speed at which nerve impulses propagate down the neural axon. By increasing the electrical resistance across the cell membrane, myelin helps prevent the electrical current from leaving the axon.

Neural demyelination is a condition characterized by a reduction of myelin protein in the nervous system, and is the basis for many neurodegenerative autoimmune diseases such as multiple sclerosis, experimental autoimmune encephalomyelitis, chronic inflammatory demyelinating polyneuropathy, progressive multifocal leukoencephalopathy, transverse myelitis, Guillain-Barré Syndrome, central pontine myelinosis, Alzheimer's Disease, progressive supenuclear palsy, multifocual motor neuropathy, and leukodystrophies such as Adrenoleukodystrophy (ALD), Alexander's Disease, Canavan Disease, Krabbe Disease, Metachromatic Leukodystrophy (MLD), Pelizaeus-Merzbacher Disease, Refsum Disease, Cockayne Syndrome, Van der Knapp Syndrome, and Zellweger Syndrome.

In particular, multiple sclerosis is the most common demyelinating disease, causing disability in many young adults. Because of demyelination and scarring, multiple sclerosis affects the ability of nerve cells in the brain and spinal cord to communicate with each other. As such, a person suffering from multiple sclerosis can exhibit a variety of neurological symptoms, including changes in sensation such as loss of sensitivity or tingling, muscle weakness, loss of coordination and paralysis. The disease generally occurs in two stages, a relapsing stage and a chronic progressive phase.

Current treatments for multiple sclerosis include anti-inflammatory and immuno-modulatory approaches. However, both are only partially effective in the relapsing stage of the disease, and little to no effect on the secondary progressive phase of the disease. Recently, estrogen receptor-β modulators have been shown to slow such neurodegeneration. Carswell, H. V. O. et al., *AJP-Heart Circ. Physiol.*, 2004, vol. 287, 1501-04; Crawford, D. K. et al., *Brain*, 2010, vol. 133, 2999-3016; Donzelli, A. et al., *J. Pharmacol. Sci.*, 2010, vol. 114, 158-167.

Therefore, a need for an effective treatment for demyelinating diseases remains. Specifically, a compound which stimulates endogenous myelination and spares axon degeneration is preferred.

FIELD OF THE INVENTION

In light of the foregoing, it is an object of the present invention to provide a method of preventing demyelination and/or enhancing remyelination of an axon of a nerve cell comprising contacting the nerve cell with an effective amount of a 6-substituted estradiol derivative. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Accordingly, in one aspect of the invention, the 6-substituted estradiol derivatives used in the methods disclosed herein are a compound of the formula I:

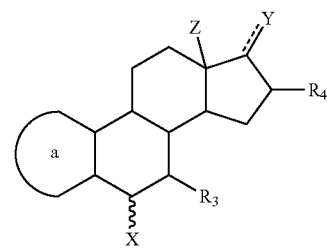

wherein the "a" ring is selected from the group consisting of

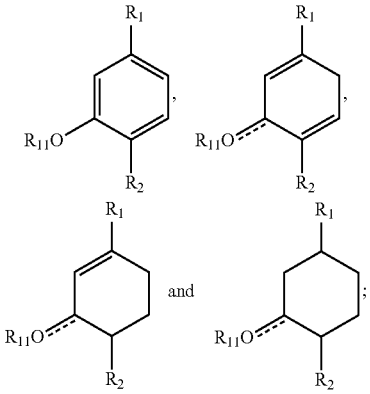

$R_1$, $R_2$, $R_3$ and $R_4$ are independently hydrogen, $C_1$-$C_6$ alkyl, halo, a sulfate, a glucuronide, —OH, a bulky group, aryl, cycloalkyl, heteroaryl, heterocycloalkyl, —N(CH$_2$)$_n$; a phosphate group, and a phosphinate group; $R_{11}$ is selected from the group consisting of H, $C_1$-$C_6$ alkyl, halogen, a sulfate, a glucoronide, —SO$_2$NH$_2$, —COOH, —CN, —CH$_2$CN—, —NHCN—, —CHO, =CHOCH$_3$, —COO salt, —OSO$_2$alkyl, —NH$_2$, and —NHCO(CH$_2$)$_n$; X is selected from the group consisting of $C_1$-$C_{12}$ alkyl, $C_2$-$C_{12}$ alkenyl, $C_2$-$C_{12}$ alkynyl, halogen, a glucoronide, —NH$_2$, —SO$_2$NH$_2$, —COOH, —CN, —CH$_2$CN, —NHCN, —CHO, —COOsalt, —OSO$_2$alkyl, —SH, —CH[(CH$_2$)$_n$CH$_3$]COOCH$_3$, —(CH$_2$)$_m$COOCH$_3$, —(CH$_2$)$_m$—O—CH$_3$, —(CH$_2$)$_m$—O—(CH$_2$)$_n$CH$_3$, (CH$_2$)$_m$—S—CH$_3$, —(CH$_2$)$_m$—S—(CH$_2$)$_n$CH$_3$, —(CH$_2$)$_m$—NH—(CH$_2$)$_n$CH$_3$, —C$_2$-C$_8$ alkenyl-O—(CH$_2$)$_n$CH$_3$, —C$_2$-C$_8$ alkenyl-S—(CH$_2$)$_n$CH$_3$, —C$_2$-C$_8$ alkenyl-N—(CH$_2$)$_n$CH$_3$, —C$_2$-C$_8$ alkynyl-O—

(CH$_2$)$_n$CH$_3$, —C$_2$-C$_8$ alkynyl-S—(CH$_2$)$_n$CH$_3$, —C$_2$-C$_8$ alkynyl-N—(CH$_2$)$_n$CH$_3$, —(CH$_2$)$_m$—OH, —(CH$_2$)$_m$—NH$_2$, —(CH$_2$)$_m$—O—NH$_2$, —(CH$_2$)$_m$—S—NH$_2$, —NH(CH$_2$)$_m$CH$_3$, —NH(CH$_2$)$_m$OCH$_3$, —NH(CH$_2$)$_m$CHOH—COOH, —N(CH$_3$)$_2$, —(CH$_2$)$_m$(NH)CH$_2$OH, —NHCOOH, —(CH$_2$)$_m$NHCOOH, —NO$_2$, —SCN, —SO$_2$alkyl, —B(OH)$_2$, —(CH$_2$)$_m$ N(CH$_3$)—SO$_2$—NH$_3$, —(CH$_2$)$_m$—NH—SO$_2$—NH$_2$, —NHC(=S)CH$_3$, and —NHNH$_2$; Y is selected from hydrogen, =O, —OCO(C$_1$-C$_{20}$ alkyl) and —OH; and Z is H or methyl; wherein m is an integer between 0-20, n is an integer between 0-8, the = symbol represents either a single or a double bond capable of forming a keto group at position 3 and/or 17; and the ∽ symbol represents any type of bond regardless of the stereochemistry; and the respective enantiomers, other stereochemical isomers, hydrates, solvates, tautomers and pharmaceutically acceptable salts of said compounds.

In another aspect of the invention, the method specifically provides for compounds that bind to one or both of estrogen receptor-α (ER-α) and estrogen receptor-β (ER-β). Such a method can comprise initiating, enhancing or increasing gene transcription for RNA encoding genes involved in key signaling pathways for differentiation of precursor or progenitor cells to cells that form myelin.

Other objects, features, benefits and advantages of the present invention will be apparent from this summary and the following descriptions of certain embodiments, and will be readily apparent to those skilled in the art having knowledge of various steroid compounds and related therapeutic methods. Such objects, features, benefits and advantages will be apparent from the above as taken into conjunction with the accompanying examples, data, figures or with consideration of the references incorporated herein.

DETAILED DESCRIPTION OF THE INVENTION

Figure 1:
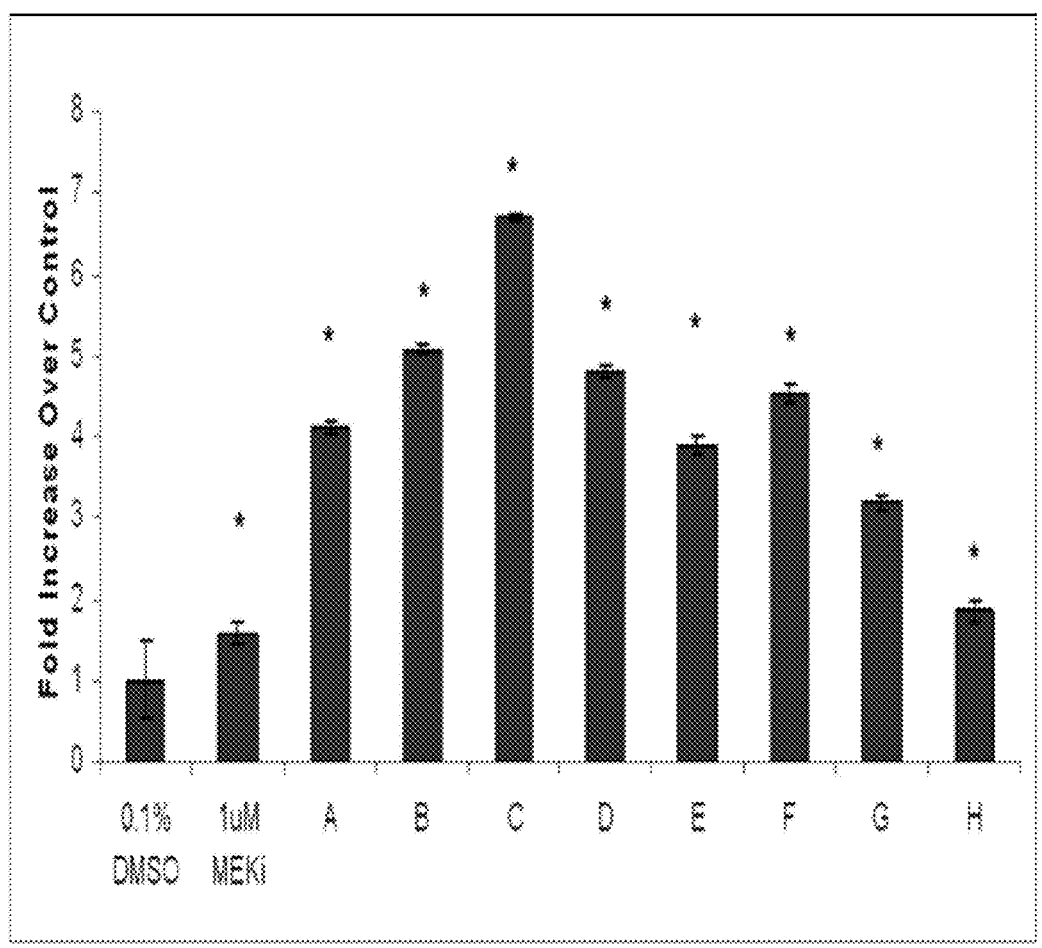
FIG. 1 shows the total number of differentiated oligodendrocyte precursor cells (OPCs) in mouse culture after 96 hours of treatment with various 6-substituted estradiol derivatives.

Unless defined otherwise, all technical and scientific terms used herein have the same meaning as is commonly understood by one of skill in the art to which this invention belongs and shall be understood to have the meanings described below. All publications and patents referred to herein are incorporated by reference in their entirety. Unless otherwise specified, a reference to a particular compound includes all such isomeric forms, including racemic and other mixtures thereof. Unless otherwise specified, a reference to a particular compound also includes ionic, salt, solvate (e.g., hydrate), protected forms, prodrugs, and other stereoisomers thereof, for example, as discussed herein.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19, and discussed herein.

The term "treatment," or "therapy" as used herein in the context of treating a condition, pertains generally to treatment and therapy of a mammalian subject, whether of a human or a non-human animal (e.g., in veterinary applications), in which some desired therapeutic effect is achieved, for example, the inhibition of the progress of the condition, and includes a reduction in the rate of progress, a halt in the rate of progress, amelioration of the condition, and/or cure of the condition. Treatment as a prophylactic measure is also included. Treatment includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), anti-inflammatory, prodrugs (e.g., employing protecting groups including phosphoric acid derivatives and phosphinates at suitable positions such as position 3 or 17, other compounds used for photodynamic therapy, GDEPT, ADEPT, etc.), surgery, radiation therapy, and gene therapy. Preferable combination treatments include the methods of the invention in combination with existing therapies for muscular sclerosis, as for example, anti-inflammatory therapy or immuno-modulatory therapy.

The term "stereochemical isomer" as used herein, refers to isomers that differ from each other only in the way the atoms are oriented in space. The two stereoisomers particularly of importance in the instant invention are enantiomers and diastereomers depending on whether or not the two isomers are mirror images of each other. In the preferred embodiment, the claimed formulations comprise such compounds that isolated, resolved and are "substantially free of other isomers."

The term "therapeutically-effective amount," as used herein, pertains to that amount of an active compound, or a material, composition or dosage form comprising an active compound, which is effective for producing some desired therapeutic effect, commensurate with a reasonable benefit/risk ratio. By the term "effective amount" is meant an amount that can bring about a detectable effect, generally.

The term "patient" or "subject" refers to animals, including mammals, preferably humans.

The term "tissue" refers generally to specialized cells which may perform a particular function. The term "tissue" may refer to an individual cell or a plurality or aggregate of cells, for example, membranes, blood or organs. The term "tissue" also includes reference to an abnormal cell or a plurality of abnormal cells. Exemplary tissues include breast tissue, including breast cells, membranous tissues, including endothelium and epithelium, laminae, connective tissue, including interstitial tissue, and tumors.

By "alkyl" in the present invention is meant a straight or branched chain alkyl radical having 1-20, and preferably from 1-12, carbon atoms. Examples include but are not limited to methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Each alkyl group may be optionally substituted with one, two or three substituents such as, for example, a halo, cycloalkyl, aryl, alkenyl or alkoxy group and the like.

By "aryl" is meant an aromatic carbocylic radical having a single ring (e.g. phenyl), multiple rings (e.g. biphenyl) or multiple fused rings in which at least one is aromatic (e.g. 1,2,3,4-tetrahydronaphthyl). The aryl group can also be optionally mono-, di-, or trisubstituted with, for example, halo, alkyl, alkenyl, cycloalkyl or alkoxy and the like.

By "heteroaryl" is meant one or multiple fused aromatic ring systems of 5-, 6- or 7-membered rings containing at least one and up to four heteroatoms selected from nitrogen, oxygen or sulfur. Examples include but are not limited to furanyl, thienyl, pyridinyl, pyrimidinyl, benzimidazolyl and benzoxazolyl. The heteroaryl group can also be optionally mono-, di-, or trisubstituted with, for example, halo, alkyl, alkenyl, cycloalkyl or alkoxy and the like.

By "cycloalkyl" is meant a carbocylic radical having a single ring (e.g. cyclohexyl), multiple rings (e.g. bicyclohexyl) or multiple fused rings (e.g.). The cycloalkyl group can optionally contain from 1 to 4 heteroatoms. In addition, the cycloalkyl group may have one or more double bonds. The cycloalkyl group can also be optionally mono-, di-, or trisubstituted with, for example, halo, alkyl, alkenyl, aryl or alkoxy and the like.

By "alkoxy" is meant an oxy-containing radical having an alkyl portion. Examples include, but are not limited to, methoxy, ethoxy, propoxy, butoxy and tert-butoxy. The alkoxy group can also be optionally mono-, di-, or trisubstituted with, for example, halo, aryl, cycloalkyl or alkoxy and the like.

By "alkenyl" is meant a straight or branched hydrocarbon radical having from 2 to 20, and preferably from 2-6, carbon atoms and from one to three double bonds and includes, for example, ethenyl, propenyl, 1-but-3-enyl, 1-pent-3-enyl, 1-hex-5-enyl. The alkenyl group can also be optionally mono-, di-, or trisubstituted with, for example, halo, aryl, cycloalkyl or alkoxy and the like.

"Halo" or "halogen" is a halogen radical of fluorine, chlorine, bromine or iodine.

By "glucuronide" is meant a glycoside radical of glucuronic acid.

The term "sulfate" refers to a radical having the general formula $-OS(O)_2-OR'$, wherein R' is hydrogen, a metal or an alkyl group.

The term "phosphate" refers to a radical having the general formula $OP(O)(OR')_2$, wherein each R' is independently hydrogen, a metal or an alkyl group.

The term "phosphinate" refers to a radical having the general formula $-OP(O)(R')_2$, wherein each R' is independently hydrogen, a metal or an alkyl group.

By "bulky group" is meant a substituent that produces steric hindrance about the space to which it is attached, e.g. a t-butyl group.

The term "amino alkyl" as used herein refers to an alkyl group with an amino group on it, for example, $H_2N-CH_2-$, $H_2N-CH_2CH_2-$, $Me_2NCH_2-$, etc., wherein the point of attachment is a carbon of the alkyl chain; and the term "alkyl amino" as used herein refers to an amino group with an alkyl group attached to the nitrogen atom, for example, CH3NH—, EtNH—, iPr-NH—, etc., wherein the point of attachment is via the nitrogen atom of the amino group. All other terms wherein successive radicals are employed will adhere to a similar rule.

In an embodiment of the invention, a method of preventing demyelination and/or enhancing/stimulating remyelination of an axon of a nerve cell comprising contacting the nerve cell with an effective amount of a 6-substituted estradiol derivative of Formula I is described. Preferably, a compound which stimulates endogenous myelination (production of the myelin sheath) and spares axon degeneration is employed. In a non-limiting example, myelination is stimulated by differentiation of precursor cells, such as for example, Schwann cell precursors or oligodendrocyte progenitor cells (OPCs), into glial cells, such as for example, Schwann cells or oligodendrocytes, respectively.

In response to demyelination, precursor/progenitor cells must undergo a switch from an essentially quiescent state to a regenerative phenotype. This activation is the first step in the remyelination process and involves the key step of up-regulation of several genes, many of which are associated with the generation of, for example, oligodendrocytes during development. Certain non-limiting examples of differentially expressed genes ($p<0.0001$) within key signaling pathways for oligodendrocyte differentiation include delta/notch-like EFG repeat (DNER), oligodendrocyte lineage transcription factor 2 (OLIG2), myelin basic protein (MBP), myelin oligodendrocyte glycoprotein (MOG), interleukin 23 receptor (IL23R), transmembrane protein 108 (TMEM108), connexin (AF251047), interleukin 20 receptor alpha (IL20RA), interleukin 28A (IL28A), homeobox protein (NKX2.2), myelin transcription factor 1-like protein (MYT1), and sex determining region Y-box 2 (SOX2), and the like. The differentiation phase encompasses three distinct steps: establishing contact with the axon that is to be remyelinated, expressing myelin genes and generating a myelin membrane, and finally wrapping and compacting the membrane to form the sheath. The 6-substituted estradiol derivatives of Formula I up-regulate these genes in signaling pathways involved in proliferation and differentiation of OPCs so that remyelination can occur. As such, the compounds of Formula I can be used to treat conditions that prevent demyelination and/or enhance/stimulate remyelination. Such a method can also include monitoring the remyelination.

Accordingly, demyelinating disorders that can be treated by the compounds of Formula I include but are not limited to, for example, multiple sclerosis (e.g., relapsing/remitting multiple sclerosis, secondary progressive multiple sclerosis, progressive relapsing multiple sclerosis, primary progressive multiple sclerosis, and acute fulminant multiple sclerosis), central pontine myelinolysis, experimental autoimmune encephalomyelitis, acute disseminated encephalomyelitis, transverse myelitis, progressive multifocal leukoencephalopathy; Alzheimer's Disease, subacute sclerosing panencephalitis, post-infectious encephalomyelitis, chronic inflammatory demyelinating polyneuropathy, progressive supernuclear palsy, multifocual motor neuropathy, Guillain-Barré Syndrome, progressive multifocal leucoencephalopathy, Devic's Disease, Balo's concentric sclerosis, and a leukodystrophy such as metachromatic leukodystrophy, Krabbe disease, Adrenoleukodystrophy (ALD), Pelizaeus-Merzbacher disease, Canavan disease, childhood ataxia with central hypomyelination, Alexander's disease, Cockayne syndrome, Van der Knapp syndrome, Zellweger syndrome and Refsum disease. A human patient having a demyelinating disorder can have one or more symptoms of a demyelinating disorder such as, but not limited to, impaired vision, numbness, weakness in extremities, tremors or spasticity, heat intolerance, speech impairment, incontinence, dizziness, or impaired proprioception (e.g., balance, coordination, sense of limb position). A human (e.g., a human patient) with a family history of a demyelinating disorder (e.g., a genetic predisposition for a demyelinating disorder), or who exhibits mild or infrequent symptoms of a demyelinating disorder described above can be, for the purposes of the method, considered at risk of developing a demyelinating disorder (e.g., multiple sclerosis). The human can be monitored for a result, e.g., an improvement in one or more symptoms of a demyelinating disorder (such as increased remyelination), e.g., any of the symptoms of demyelinating disorders described herein.

In an embodiment of the present invention, compounds of the methods have the general structure shown in Formula (Ia) below:

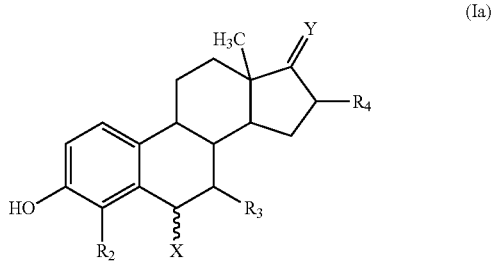

(Ia)

wherein $R_2$, $R_3$, $R_4$, X and Y are as defined above for Formula (I). Even more preferably, Y is selected from =O and —OH; $R_4$ is selected from hydrogen, halo and $C_1$-$C_6$ alkyl; $R_2$ is selected from hydrogen, —OH and halo; $R_3$ is selected from hydrogen, halo and —OH; and X is selected from $C_1$-$C_{12}$ alkyl, $C_2$-$C_{12}$ alkenyl, —$(CH_2)_m COOCH_3$, —$(CH_2)_m$—O—$CH_3$, —$(CH_2)_m$—O—$(CH_2)_n CH_3$, $(CH_2)_m$—S—$CH_3$, —$(CH_2)_m$—S—$(CH_2)_n CH_3$, —$(CH_2)_m$—N—$(CH_2)_n CH_3$, —$C_2$-$C_8$ alkenyl-O—$(CH_2)_n CH_3$, —$C_2$-$C_8$ alkenyl-S—$(CH_2)_n CH_3$, —$C_2$-$C_8$ alkenyl-N—$(CH_2)_n CH_3$, —$C_2$-$C_8$ alkynyl-O—$(CH_2)_n CH_3$, —$C_2$-$C_8$ alkynyl-S—$(CH_2)_n CH_3$, —$C_2$-$C_8$ alkynyl-N—$(CH_2)_n CH_3$, —$(CH_2)_m$—OH, —$(CH_2)_m$—O—$NH_2$, —$(CH_2)_m$—S—$NH_2$, —NH$(CH_2)_m CH_3$, —NH$(CH_2)_m OCH_3$, —NH$(CH_2)_m$CHOH—COOH, —$(CH_2)_m$(NH)$CH_2$OH, —$(CH_2)_m$NHCOOH, —$(CH_2)_m$N$(CH_3)$—$SO_2$—$NH_3$, and —$(CH_2)_m$—NH—$SO_2$—$NH_2$; m is an integer from 1-20; n is an integer from 0-8; and the $=\!=\!=$ symbol represents either a single or a double bond. Yet even more preferably, Y is (S)—OH; $R_4$ is selected from hydrogen or alkyl; $R_2$ is hydrogen; $R_3$ is hydrogen; and X is selected from $C_1$-$C_{12}$ alkyl, $C_2$-$C_{12}$ alkenyl, —$(CH_2)_m$—O—$CH_3$, —$(CH_2)_m$—O—$(CH_2)_n CH_3$, $(CH_2)_m$—S—$CH_3$, and —$(CH_2)_m$—S—$(CH_2)_n CH_3$; m is an integer from 1-12; n is an integer from 0-4; and the C-13 methyl is in the (S) configuration.

Yet another embodiment of the present invention is directed to methods using compounds of a Formula (Ib):

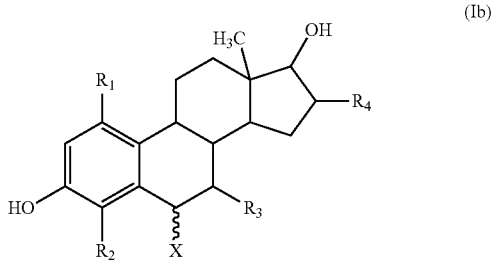

(Ib)

wherein $R_1$, $R_2$, $R_3$, $R_4$ and X are as defined above for Formula (I). Even more preferably, $R_1$ is selected from hydrogen, —OH and halo; $R_4$ is selected from hydrogen, halo and $C_1$-$C_6$ alkyl; $R_2$ is selected from hydrogen and halo; $R_3$ is selected from hydrogen, halo and —OH; and X is selected from $C_1$-$C_{12}$ alkyl, $C_2$-$C_{12}$ alkenyl, —$(CH_2)_m COOCH_3$, —$(CH_2)_m$—O—$CH_3$, —$(CH_2)_m$—O—$(CH_2)_n CH_3$, $(CH_2)_m$—S—$CH_3$, —$(CH_2)_m$—S—$(CH_2)_n CH_3$, —$(CH_2)_m$—N—$(CH_2)_n CH_3$, —$C_2$-$C_8$ alkenyl-O—$(CH_2)_n CH_3$, —$C_2$-$C_8$ alkenyl-S—$(CH_2)_n CH_3$, —$C_2$-$C_8$ alkenyl-N—$(CH_2)_n CH_3$, —$C_2$-$C_8$ alkynyl-O—$(CH_2)_n CH_3$, —$C_2$-$C_8$ alkynyl-S—$(CH_2)_n CH_3$, —$C_2$-$C_8$ alkynyl-N—$(CH_2)_n CH_3$, —$(CH_2)_m$—OH, —$(CH_2)_m$—O—$NH_2$, —$(CH_2)_m$—S—$NH_2$, —NH$(CH_2)_m CH_3$, NH$(CH_2)_m OCH_3$, —NH$(CH_2)_m$CHOH—COOH, —$(CH_2)_m$(NH)$CH_2$OH, —$(CH_2)_m$N-HCOOH, —$(CH_2)_m$N$(CH_3)$—$SO_2$—$NH_3$, and —$(CH_2)_m$—NH—$SO_2$—$NH_2$; m is an integer from 1-20; and n is an integer from 0-8. Yet even more preferably, $R_1$ is hydrogen; $R_4$ is selected from hydrogen or alkyl; $R_2$ is hydrogen; $R_3$ is hydrogen; and X is selected from $C_1$-$C_{12}$ alkyl, $C_2$-$C_{12}$ alkenyl, —$(CH_2)_m$—O—$CH_3$, —$(CH_2)_m$—O—$(CH_2)_n CH_3$, $(CH_2)_m$—S—$CH_3$, and —$(CH_2)_m$—S—$(CH_2)_n CH_3$; m is an integer from 1-12; n is an integer from 0-4; and both the C-13 methyl and C-17 hydroxyl are in the (S) configuration.

Still another embodiment of the invention is directed to methods using a compound of a Formula (Ic):

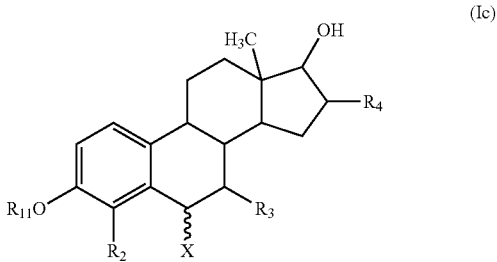

(Ic)

wherein $R_{11}$, $R_2$, $R_3$, $R_4$ and X are as defined above for Formula (I). Even more preferably, $R_{11}$ is hydrogen or $C_1$-$C_6$ alkyl; $R_4$ is selected from hydrogen, halo and $C_1$-$C_6$ alkyl; $R_2$ is selected from hydrogen and halo; $R_3$ is selected from hydrogen, halo and —OH; and X is selected from $C_1$-$C_{12}$ alkyl, $C_2$-$C_{12}$ alkenyl, —$(CH_2)_m COOCH_3$, —$(CH_2)_m$—O—$CH_3$, —$(CH_2)_m$—O—$(CH_2)_n CH_3$, $(CH_2)_m$—S—$CH_3$, —$(CH_2)_m$—S—$(CH_2)_n CH_3$, —$(CH_2)_m$—N—$(CH_2)_n CH_3$, —$C_2$-$C_8$ alkenyl-O—$(CH_2)_n CH_3$, —$C_2$-$C_8$ alkenyl-S—$(CH_2)_n CH_3$, —$C_2$-$C_8$ alkenyl-N—$(CH_2)_n CH_3$, —$C_2$-$C_8$ alkynyl-O—$(CH_2)_n CH_3$, —$C_2$-$C_8$ alkynyl-S—$(CH_2)_n CH_3$, —$C_2$-$C_8$ alkynyl-N—$(CH_2)_n CH_3$, —$(CH_2)_m$—OH, —$(CH_2)_m$—O—$NH_2$, —$(CH_2)_m$—S—$NH_2$, —NH$(CH_2)_m CH_3$, NH$(CH_2)_m OCH_3$, —NH$(CH_2)_m$CHOH—COOH, —$(CH_2)_m$(NH)$CH_2$OH, —$(CH_2)_m$NHCOOH, —$(CH_2)_m$N$(CH_3)$—$SO_2$—$NH_3$, and —$(CH_2)_m$—NH—$SO_2$—$NH_2$; m is an integer from 1-20; and n is an integer from 0-8. Yet even more preferably, $R_{11}$ is hydrogen; $R_4$ is selected from hydrogen or alkyl; $R_2$ is hydrogen; $R_3$ is hydrogen; and X is selected from $C_1$-$C_{12}$ alkyl, $C_2$-$C_{12}$ alkenyl, —$(CH_2)_m$—O—$CH_3$, —$(CH_2)_m$—O—$(CH_2)_n CH_3$, $(CH_2)_m$—S—$CH_3$, and —$(CH_2)_m$—S—$(CH_2)_n CH_3$; m is an integer from 1-12; n is an integer from 0-4; and both the C-13 methyl and C-17 hydroxyl are in the (S) configuration.

Yet another embodiment of the present invention is directed to methods using a compound of a Formula (Id):

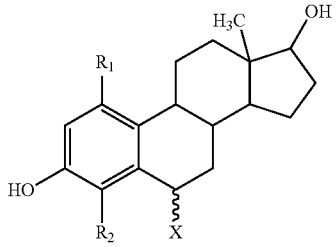

(Id)

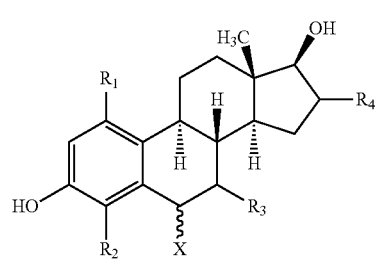

(If)

wherein $R_1$, $R_2$, and X are as defined above for Formula (I). Even more preferably, $R_1$ is selected from hydrogen, —OH and halo; $R_2$ is selected from hydrogen and halo; and X is selected from $C_1$-$C_{12}$ alkyl, $C_2$-$C_{12}$ alkenyl, —$(CH_2)_m$COOCH$_3$, —$(CH_2)_m$—O—CH$_3$, —$(CH_2)_m$—O—$(CH_2)_n$CH$_3$, $(CH_2)_m$—S—CH$_3$, —$(CH_2)_m$—S—$(CH_2)_n$CH$_3$, —$(CH_2)_m$—N—$(CH_2)_n$C$_3$, —$C_2$-$C_8$ alkenyl-O—$(CH_2)_n$CH$_3$, —$C_2$-$C_8$ alkenyl-S—$(CH_2)_n$CH$_3$, —$C_2$-$C_8$ alkenyl-N—$(CH_2)_n$CH$_3$, —$C_2$-$C_8$ alkynyl-O—$(CH_2)_n$CH$_3$, —$C_2$-$C_8$ alkynyl-S—$(CH_2)_n$CH$_3$, —$C_2$-$C_8$ alkynyl-N—$(CH_2)_n$CH$_3$, —$(CH_2)_m$—OH, —$(CH_2)_m$—O—NH$_2$, —$(CH_2)_m$—S—NH$_2$, —NH$(CH_2)_m$CH$_3$, NH$(CH_2)_m$OCH$_3$, —NH$(CH_2)_m$CHOH—COOH, —$(CH_2)_m$(NH)CH$_2$OH, —$(CH_2)_m$N-HCOOH, —$(CH_2)_m$ N(CH$_3$)—SO$_2$—NH$_3$, and —$(CH_2)_m$—NH—SO$_2$—NH$_2$; X is selected from $C_1$-$C_{12}$ alkyl, $C_2$-$C_{12}$ alkenyl, —$(CH_2)_m$—O—CH$_3$, —$(CH_2)_m$—O—$(CH_2)_n$CH$_3$, $(CH_2)_m$—S—CH$_3$, and —$(CH_2)_m$—S—$(CH_2)_n$CH$_3$; m is an integer from 1-20; and n is an integer from 0-8. Still even more preferably, $R_1$ and $R_2$ are hydrogen; m is an integer from 1-12; n is an integer from 0-4; and both the C-13 methyl and C-17 hydroxyl are in the (S) configuration.

Yet another embodiment of the present invention is directed to methods using a compound of a Formula (Ie):

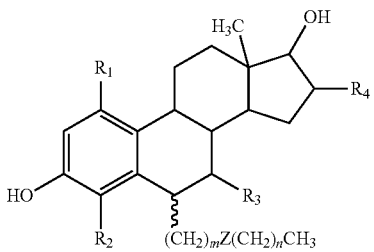

(Ie)

wherein m, n, $R_1$, $R_2$, $R_3$ and $R_4$ are as defined above for Formula (I), and Z is selected from —O—, —S— and —NH—. Even more preferably, m is 1-12, n is 0-4, $R_1$ is selected from hydrogen, —OH and halo; $R_4$ is selected from hydrogen, halo and $C_1$-$C_6$ alkyl; $R_2$ is selected from hydrogen and halo; $R_3$ is selected from hydrogen, halo and OH; Z is selected from —O— and —S—; and both the C-13 methyl and C-17 hydroxyl are in the (S) configuration.

Still another embodiment of the present invention is directed to methods using a compound of a Formula (If):

wherein $R_1$, $R_2$, $R_3$, $R_4$ and X are as defined above for Formula (I). Even more preferably, $R_1$ is selected from hydrogen, —OH and halo; $R_4$ is selected from hydrogen, halo and $C_1$-$C_6$ alkyl; $R_2$ is selected from hydrogen and halo; $R_3$ is selected from hydrogen, halo and —OH; and X is selected from $C_1$-$C_{12}$ alkyl, $C_2$-$C_{12}$ alkenyl, —$(CH_2)_m$COOCH$_3$, —$(CH_2)_m$—O—CH$_3$, —$(CH_2)_m$—O—$(CH_2)_n$CH$_3$, $(CH_2)_m$—S—CH$_3$, —$(CH_2)_m$—S—$(CH_2)_n$CH$_3$, —$(CH_2)_m$—N—$(CH_2)_n$CH$_3$, —$C_2$-$C_8$ alkenyl-O—$(CH_2)_n$CH$_3$, —$C_2$-$C_8$ alkenyl-S—$(CH_2)_n$CH$_3$, —$C_2$-$C_8$ alkenyl-N—$(CH_2)_n$CH$_3$, —$C_2$-$C_8$ alkynyl-O—$(CH_2)_n$CH$_3$, —$C_2$-$C_8$ alkynyl-S—$(CH_2)_n$CH$_3$, —$C_2$-$C_8$ alkynyl-N—$(CH_2)_n$CH$_3$, —$(CH_2)_m$—OH, —$(CH_2)_m$—O—NH$_2$, —$(CH_2)_m$—S—NH$_2$, —NH$(CH_2)_m$CH$_3$, NH$(CH_2)_m$OCH$_3$, —NH$(CH_2)_m$CHOH—COOH, —$(CH_2)_m$(NH)CH$_2$OH, —$(CH_2)_m$N-HCOOH, —$(CH_2)_m$ N(CH$_3$)—SO$_2$—NH$_3$, and —$(CH_2)_m$—NH—SO$_2$—NH$_2$; X is selected from $C_1$-$C_{12}$ alkyl, $C_2$-$C_{12}$ alkenyl, —$(CH_2)_m$—O—CH$_3$, —$(CH_2)_m$—O—$(CH_2)_n$CH$_3$, $(CH_2)_m$—S—CH$_3$, and —$(CH_2)_m$—S—$(CH_2)_n$CH$_3$; m is an integer from 1-20; and n is an integer from 0-8. Still even more preferably, $R_1$, $R_2$, $R_3$ and $R_4$ are hydrogen; m is an integer from 1-12; and n is an integer from 0-4.

Still another embodiment of the present invention is directed to methods using a compound of a Formula (Ig):

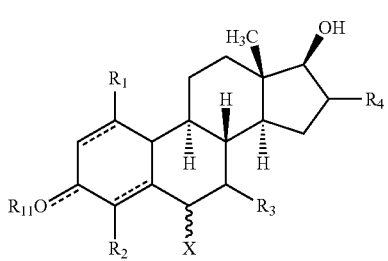

(Ig)

wherein $R_1$, $R_2$, $R_3$, $R_4$, $R_{11}$ and X are as defined above for Formula (I). Even more preferably, $R_1$ is selected from hydrogen, —OH and halo; $R_4$ is selected from hydrogen, halo and $C_1$-$C_6$ alkyl; $R_2$ is selected from hydrogen and halo; $R_3$ is selected from hydrogen, halo and —OH; and X is selected from $C_1$-$C_{12}$ alkyl, $C_2$-$C_{12}$ alkenyl, —$(CH_2)_m$COOCH$_3$, —$(CH_2)_m$—O—CH$_3$, —$(CH_2)_m$—O—$(CH_2)_n$CH$_3$, $(CH_2)_m$—S—CH$_3$, —$(CH_2)_m$—S—$(CH_2)_n$CH$_3$, —$(CH_2)_m$—N—$(CH_2)_n$CH$_3$, —$C_2$-$C_8$ alkenyl-O—$(CH_2)_n$CH$_3$, —$C_2$-$C_8$ alkenyl-S—$(CH_2)_n$CH$_3$, —$C_2$-$C_8$ alkenyl-N—$(CH_2)_n$CH$_3$, —$C_2$-$C_8$ alkynyl-O—$(CH_2)_n$CH$_3$, —$C_2$-$C_8$ alkynyl-S—$(CH_2)_n$CH$_3$, —$C_2$-$C_8$ alkynyl-N—$(CH_2)_n$CH$_3$, —$(CH_2)_m$—OH, —$(CH_2)_m$—O—NH$_2$, —$(CH_2)_m$—S—NH$_2$, —NH$(CH_2)_m$CH$_3$, NH$(CH_2)_m$OCH$_3$, —NH$(CH_2)_m$CHOH—COOH, —$(CH_2)_m$(NH)CH$_2$OH, —$(CH_2)_m$N-HCOOH, —$(CH_2)_m$ N(CH$_3$)—SO$_2$—NH$_3$, and —$(CH_2)_m$—

NH—SO$_2$—NH$_2$; X is selected from C$_1$-C$_{12}$ alkyl, C$_2$-C$_{12}$ alkenyl, —(CH$_2$)$_m$—O—CH$_3$, —(CH$_2$)$_m$—O—(CH$_2$)$_n$CH$_3$, —(CH$_2$)$_m$—S—CH$_3$, and —(CH$_2$)$_m$—S—(CH$_2$)$_n$CH$_3$; m is an integer from 1-20; ═ OR$_{11}$ is either ═O or —OH; and n is an integer from 0-8. Still even more preferably, R$_1$, R$_2$, R$_3$ and R$_4$ are hydrogen; m is an integer from 1-12; and n is an integer from 0-4.

Specific examples of compounds of Formula (I) and (Ia)-(If) are shown below:

1
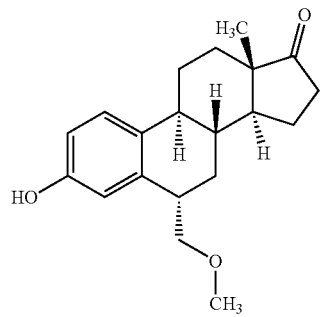

2
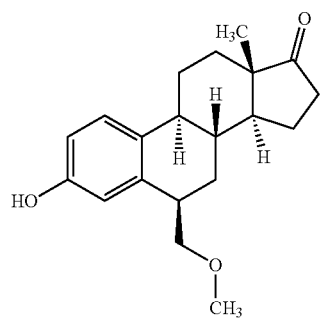

3
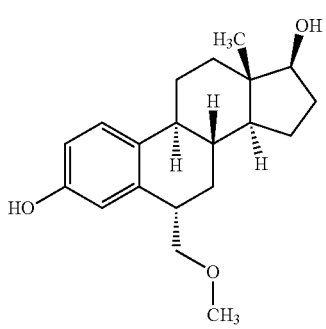

4
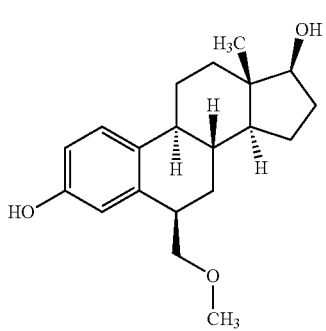

-continued

5
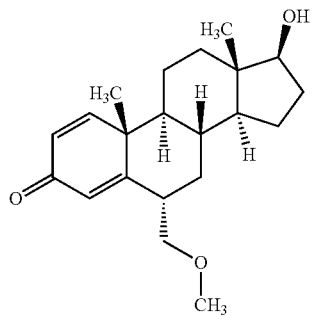

6
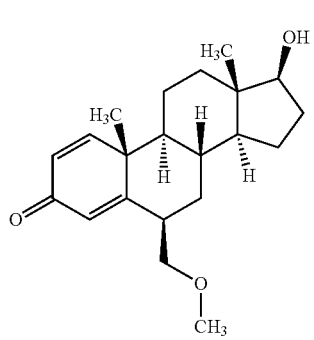

7
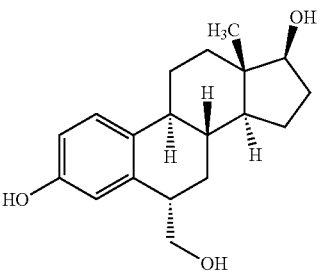

8
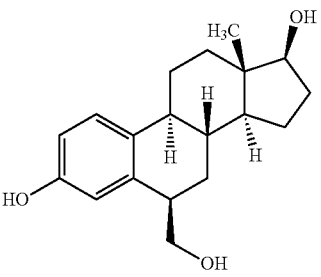

9
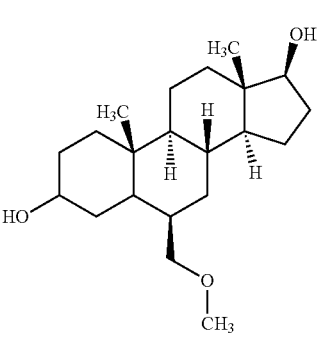

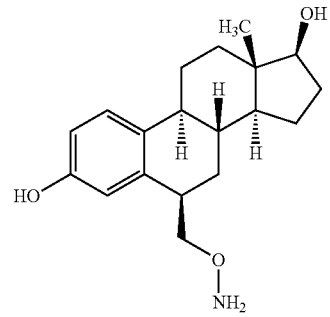
10
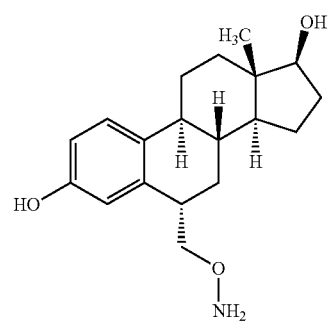
11
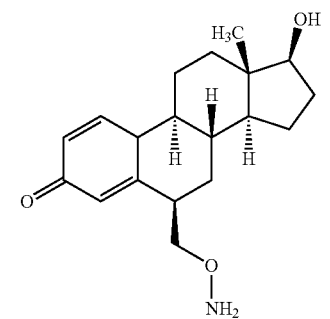
12
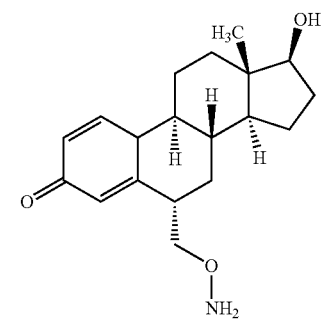
13
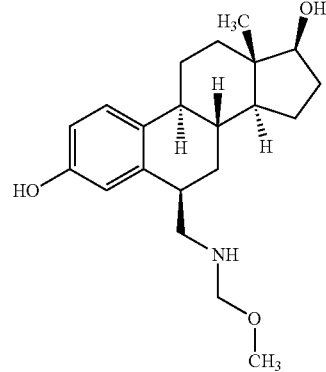
14
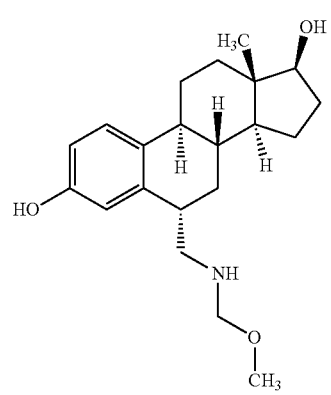
15
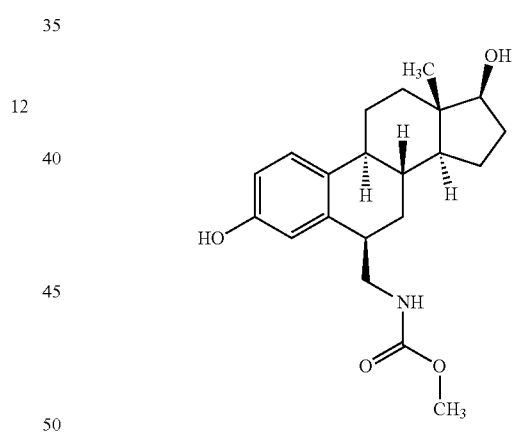
16
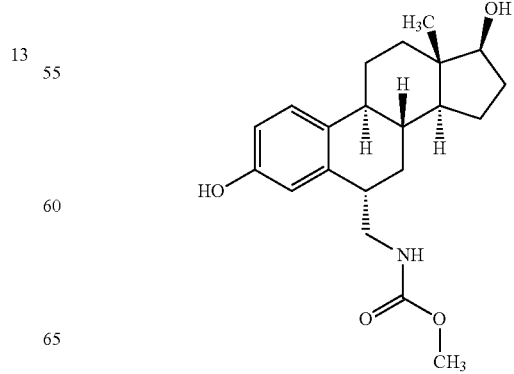
17

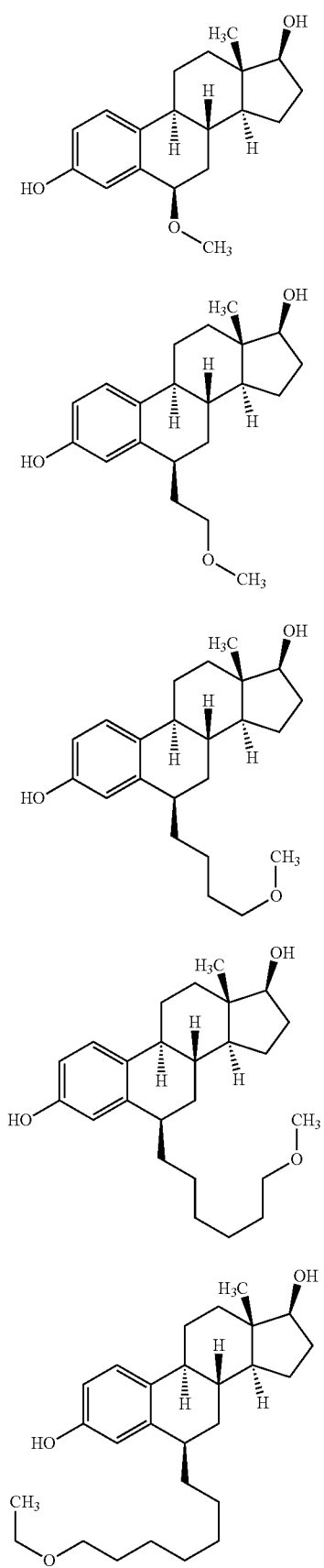
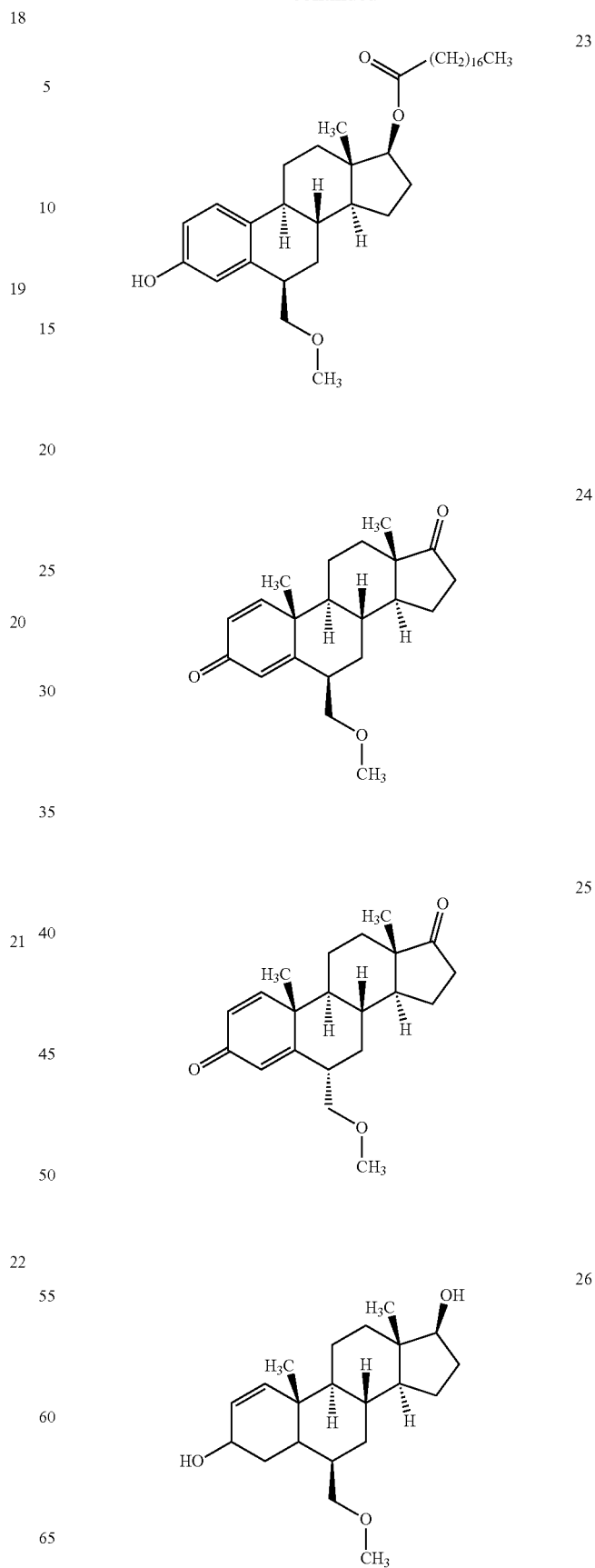

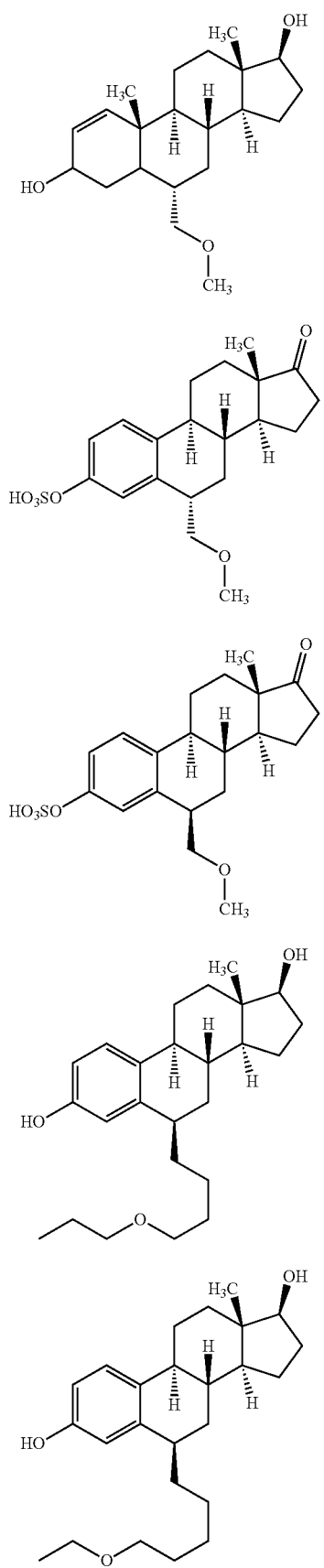
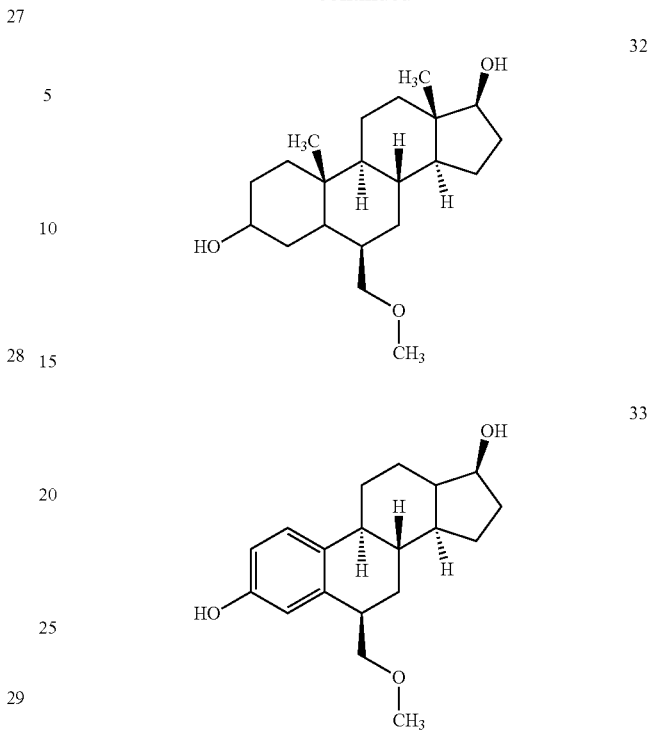

Embodiment compounds of the present invention can be used in a pharmaceutical composition. Such a composition can comprise one or more compounds selected from those discussed above, illustrated below or otherwise inferred herein, and combinations thereof. In certain embodiments, such a composition can comprise a pharmaceutically-acceptable carrier component. Without limitation, such a composition can comprise a racemic mixture of compounds. In certain embodiments, such a compound can be present as the S and R enantiomer, preferably its isolated and purified form which is substantially free of the other isomer.

The compounds of the present invention may have asymmetric centers and may occur as a racemate, a racemic mixture or as individual and purified diastereomers or enantiomers such as (named via ChemDraw Ultra, Version 11.0(3) or 12.0) (6S,8R,9S,13S,14S)-3-hydroxy-6-(methoxymethyl)-13-methyl-7,8,9,11,12,13,15,16-octahydro-6H-cyclopenta[a]phenanthren-17(14H)-one (compound 1); (6R,8R,9S,13S,14S)-3-hydroxy-6-(methoxymethyl)-13-methyl-7,8,9,11,12,13,15,16-octahydro-6H-cyclopenta[a]phenanthren-17(14H)-one (compound 2); (6S,8R,9S,13S,14S)-6-(methoxymethyl)-13-methyl-7,8,9,11,12,13,14,15,16,17-decahydro-6H-cyclopenta[a]phenanthrene-3,17-diol (compound 3); (6R,8R,9S,13S,14S)-6-(methoxymethyl)-13-methyl-7,8,9,11,12,13,14,15,16,17-decahydro-6H-cyclopenta[a]phenanthrene-3,17-diol (compound 4); (6S,8R,9S,10R,13S,14S)-17-hydroxy-6-(methoxymethyl)-10,13-dimethyl-6,7,8,9,10,11,12,13,14,15,16,17-dodecahydro-3H-cyclopenta[a]phenanthren-3-one (compound 5); (6R,8R,9S,10R,13S,14S)-17-hydroxy-6-(methoxymethyl)-10,13-dimethyl-6,7,8,9,10,11,12,13,14,15,16,17-dodecahydro-3H-cyclopenta[a]phenanthren-3-one (compound 6); (6S,8R,9S,13S,14S)-6-(hydroxymethyl)-13- methyl-7,8,9,11,12,13,14,15,16,17-decahydro-6H-cyclopenta[a]phenanthrene-3,17-diol (compound 7); (6R,8R,9S,13S,14S)-6-(hydroxymethyl)-13-methyl-7,8,9,11,12,13,14,15,16,17-decahydro-6H-cyclopenta[a]phenanthrene-3,17-diol (compound 8); (6R,8R,9S,10R,13S,14S)-6-(methoxymethyl)-10,13-dimethylhexadecahydro-1H-cyclopenta[a]phenanthrene-3,17-diol (compound 9); (6R,8R,9S,13S,14S)-6-((aminooxy)methyl)-13-methyl-7,8,9,11,12,13,14,15,16,17-decahydro-6H-cyclopenta[a]phenanthrene-3,17-diol (compound 10); (6S,8R,9S,13S,14S)-6-((aminooxy)methyl)-13-methyl-7,8,9,11,12,13,14,15,16,17-decahydro-6H-cyclopenta[a]phenanthrene-3,17-diol (compound 11); (6R,8R,9S,13S,14S)-6-((aminooxy)methyl)-17-hydroxy-13-methyl-6,7,8,9,10,11,12,13,14,15,16,17-dodecahydro-3H-cyclopenta[a]phenanthren-3-one (compound 12); (6S,8R,9S,13S,14S)-6-((aminooxy)methyl)-17-hydroxy-13-methyl-6,7,8,9,10,11,12,13,14,15,16,17-dodecahydro-3H-cyclopenta[a]phenanthren-3-one (compound 13); (6R,8R,9S,13S,14S)-6-(((methoxymethyl)amino)methyl)-13-methyl-7,8,9,11,12,13,14,15,16,17-decahydro-6H-cyclopenta[a]phenanthrene-3,17-diol (compound 14); (6S,8R,9S,13S,14S)-6-(((methoxymethyl)amino)methyl)-13-methyl-7,8,9,11,12,13,14,15,16,17-decahydro-6H-cyclopenta[a]phenanthrene-3,17-diol (compound 15); 1-((((6R,8R,9S,13S,14S)-3,17-dihydroxy-13-methyl-7,8,9,11,12,13,14,15,16,17-decahydro-6H-cyclopenta[a]phenanthren-6-yl)methyl)amino)propan-2-one (compound 16); 1-((((6S,8R,9S,13S,14S)-3,17-dihydroxy-13-methyl-7,8,9,11,12,13,14,15,16,17-decahydro-6H-cyclopenta[a]phenanthren-6-yl)methyl)amino)propan-2-one (compound 17); (6R,8R,9S,13S,14S)-6-methoxy-13-methyl-7,8,9,11,12,13,14,15,16,17-decahydro-6H-cyclopenta[a]phenanthrene-3,17-diol (compound 18); (6S,8R,9S,13S,14S)-6-(2-methoxyethyl)-13-methyl-7,8,9,11,12,13,14,15,16,17-decahydro-6H-cyclopenta[a]phenanthrene-3,17-diol (compound 19); (6R,8R,9S,13S,14S)-6-(4-methoxybutyl)-13-methyl-7,8,9,11,12,13,14,15,16,17-decahydro-6H-cyclopenta[a]phenanthrene-3,17-diol (compound 20); (6R,8R,9S,13S,14S)-6-(6-methoxyhexyl)-13-methyl-7,8,9,11,12,13,14,15,16,17-decahydro-6H-cyclopenta[a]phenanthrene-3,17-diol (compound 21); (6R,8R,9S,13S,14S)-6-(6-methoxyoctyl)-13-methyl-7,8,9,11,12,13,14,15,16,17-decahydro-6H-cyclopenta[a]phenanthrene-3,17-diol (compound 22); (6R,8R,9S,13S,14S)-3-hydroxy-6-(methoxymethyl)-13-methyl-7,8,9,11,12,13,14,15,16,17-decahydro-6H-cyclopenta[a]phenanthren-17-yl stearate (compound 23); (6R,8R,9S,10R,13S,14S)-6-(methoxymethyl)-10,13-dimethyl-7,8,9,10,11,12,13,14,15,16-decahydro-3H-cyclopenta[a]phenanthrene-3,17(6H)-dione (compound 24); (6S,8R,9S,10R,13S,14S)-6-(methoxymethyl)-10,13-dimethyl-7,8,9,10,11,12,13,14,15,16-decahydro-3H-cyclopenta[a]phenanthrene-3,17(6H)-dione (compound 25); (6R,8R,9S,10R,13S,14S)-6-(methoxymethyl)-10,13-dimethyl-4,5,6,7,8,9,10,11,12,13,14,15,16,17-tetradecahydro-3H-cyclopenta[a]phenanthrene-3,17-diol (compound 26); (6S,8R,9S,10R,13S,14S)-6-(methoxymethyl)-10,13-dimethyl-4,5,6,7,8,9,10,11,12,13,14,15,16,17-tetradecahydro-3H-cyclopenta[a]phenanthrene-3,17-diol (compound 27); (6S,8R,9S,13S,14S)-6-(methoxymethyl)-13-methyl-17-oxo-7,8,9,11,12,13,14,15,16,17-decahydro-6H-cyclopenta[a]phenanthren-3-yl hydrogen sulfate (compound 28); (6R,8R,9S,13S,14S)-6-(methoxymethyl)-13-methyl-17-oxo-7,8,9,11,12,13,14,15,16,17-decahydro-6H-cyclopenta[a]phenanthren-3-yl hydrogen sulfate (compound 29); (6R,8R,9S,13S,14S)-13-methyl-6-(4-propoxybutyl)-7,8,9,11,12,13,14,15,16,17-decahydro-6H-cyclopenta[a]phenanthrene-3,17-diol (compound 30); (6R,8R,9S,13S,14S)-13-methyl-6-(5-ethoxypentyl)-7,8,9,11,12,13,14,15,16,17-decahydro-6H-cyclopenta[a]phenanthrene-3,17-diol (compound 31); (6R,8R,9S,10R,13S,14S)-6-(methoxymethyl)-10,13-dimethylhexadecahydro-1H-cyclopenta[a]phenanthrene-3,17-diol (compound 32); and (6R,8S,9S,14S,17S)-6-(methoxymethyl)-7,8,9,11,12,13,14,15,16,17-decahydro-6H-cyclopenta[a]phenanthrene-3,17-diol (compound 33).

The compounds of the methods of the invention are prepared as described in U.S. Ser. No. 12/627,874 (incorporated herein by reference) and pertain to a method for preparing a 6-hydroxymethyl, 6-alkoxyalkyl, 6-alkylthioalkyl, 6-aminomethoxy, 6-methylaminomethoxy, or 6-methoxyamine derivatives of estradiol. Reaction schemes for preparing estradiol derivatives is given below, Schemes 1-3. Such methods can comprise reaction of a t-butyldimethylsilyl derivative of estradiol with LIDAKOR/THF/formaldehyde to obtain a 6hydroxylated compound followed by such steps as: (i) hydrolysis to obtain 6-hydroxymethyl derivative of estradiol; and/or (ii) treatment with dimethylsulfate followed by hydrolysis to obtain 6-methyloxymethyl derivative of estradiol. Compound 1 can be obtained by further oxidation of compound 3 at the C-17 hydroxyl position. Compound 33 and other dimethyl compounds can be prepared according to U.S. Ser. No. 13/232,798 (incorporated herein by reference).

In an alternative approach, the compounds of the present invention can also be prepared by a method comprising such steps as: (i) protecting an estrodial compound, (ii) acylating the protected estradiol compound at the benzylic 6-position with LIDAKOR/Butyl-Lithium/Diisopropylamine/potassium tert-amylate, (iii) reducing the position 6 aldehyde with lithium aluminum hydride, (iv) deprotecting the protected regions of the estradiol compound. A reaction scheme for preparing estradiol derivatives is given below in Scheme 2.

The compounds of the present invention can be synthesized by the following methods as depicted in the schemes below.

Scheme 1
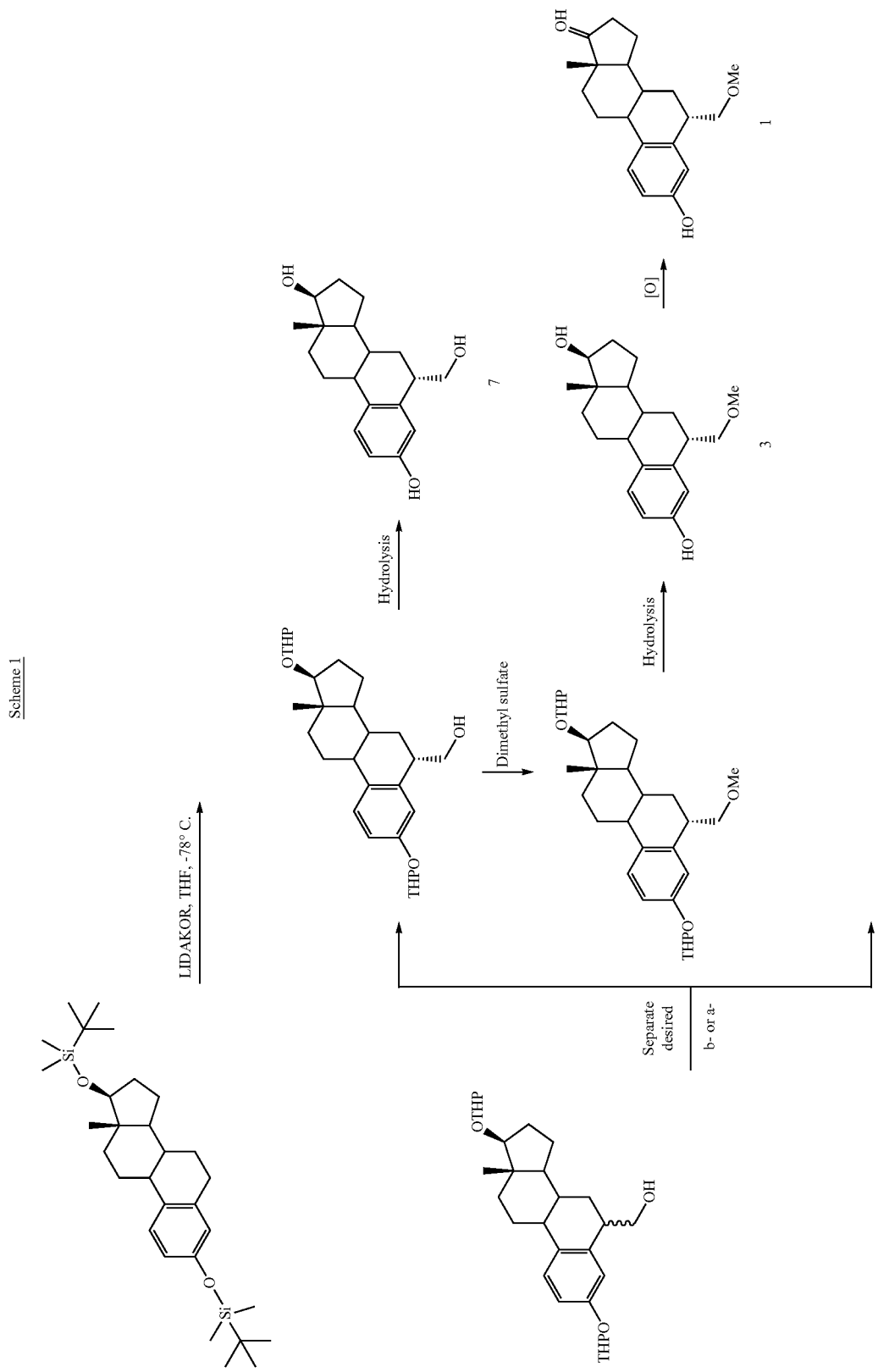

-continued
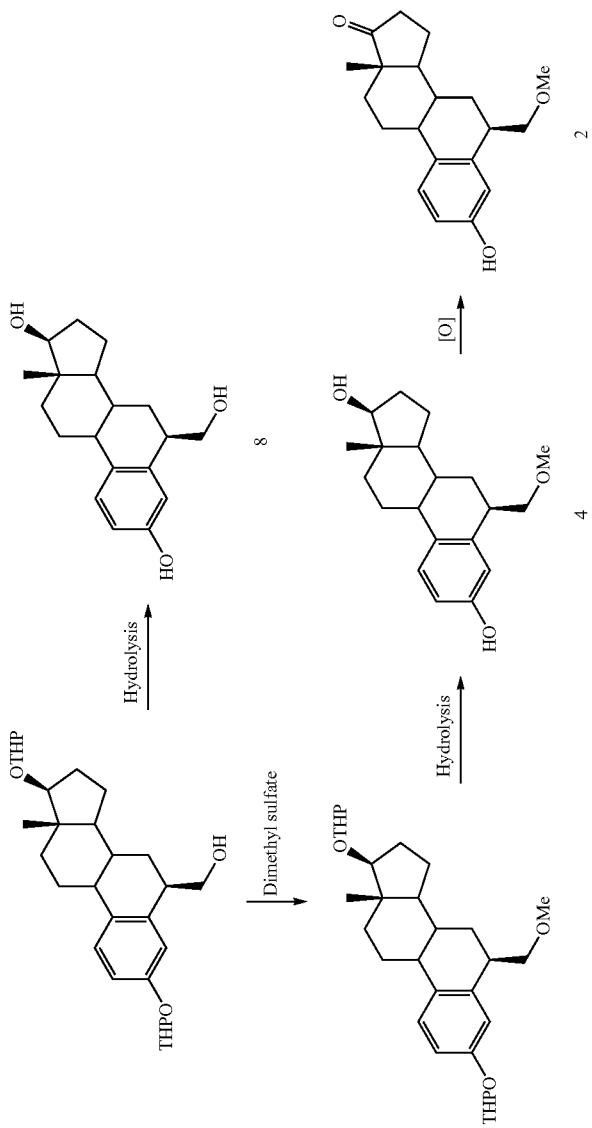

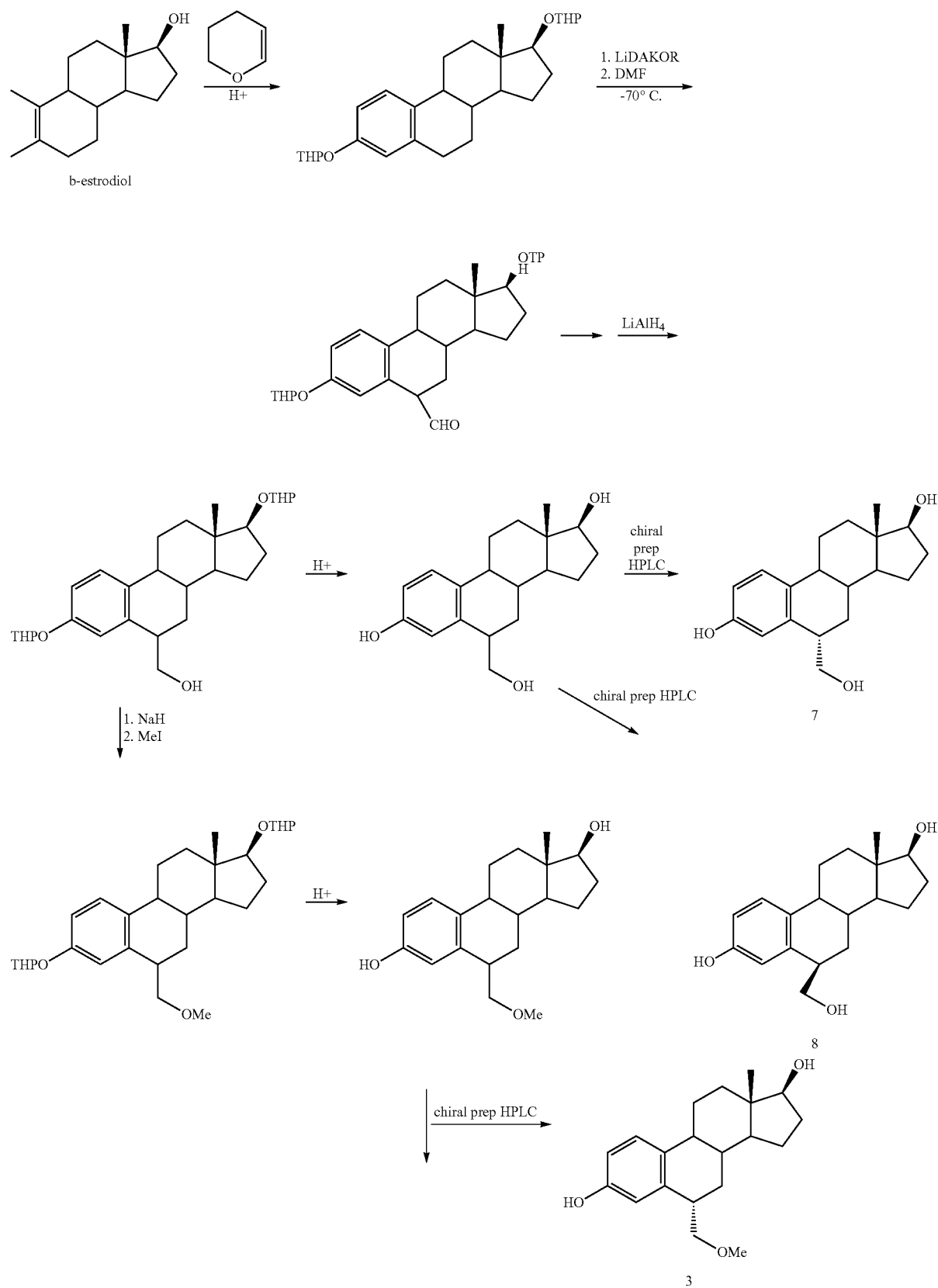
Scheme 2

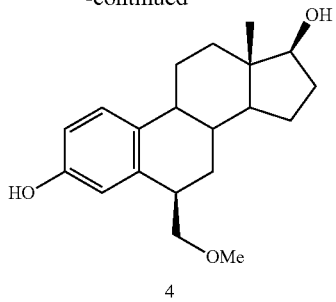

Various alkyloxyalkyl derivatives, in accordance with this invention, involve selection of alkylating agents. Such derivatives would be understood by those skilled in art made aware of this invention, and is available through synthetic procedures of the sort described herein. Accordingly, without limitation, various $C_1$ to $C_6$ alkyl and substituted alkyl reagents can be used as described herein to prepare the corresponding alkyloxyalkyl derivatives.

In another aspect of the invention, methods of making 6-amino derivatives of the estradiol are disclosed in reaction schemes below. Accordingly, 6-methoxylated estradiols described in Schemes 1-2 are employed and converted to their respective amino derivatives.

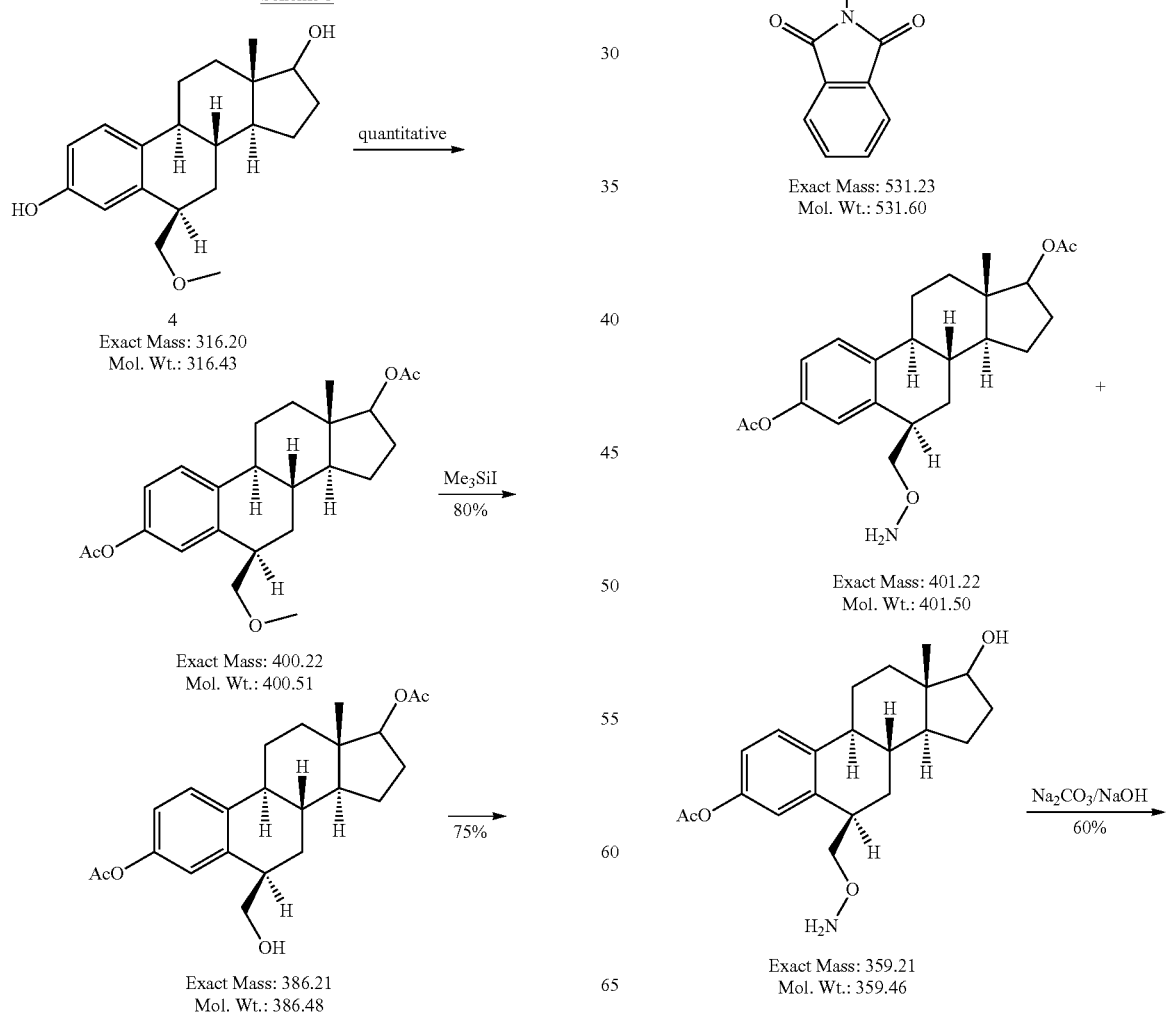

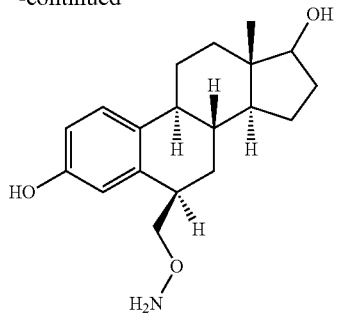

Exact Mass: 317.20
Mol. Wt.: 317.42

Methods and compounds for preventing demyelination and/or enhancing remyelination are provided. In an aspect of the invention, a method for initiating, enhancing or increasing gene transcription for RNA encoding the myelin basic protein gene and/or the myelin oligodendrocyte glycoprotein gene in a cell is provided, comprising contacting the cell with an effective amount of a 6-substituted estradiol derivative selected from Formulas (I) and (Ia) to (If). It is to be understood that such initiating, enhancing or increasing of gene transcription can occur for one or more of these genes.

As noted herein, the salts of the compounds of this invention refer to non-toxic "pharmaceutically acceptable salts." Other salts may, however, be useful in the preparation of the compounds according to the invention or of their pharmaceutically acceptable salts. When the compounds of the present invention contain a basic group, salts encompassed within the term "pharmaceutically acceptable salts" refer to non-toxic salts which are generally prepared by reacting the free base with a suitable organic or inorganic acid. Representative salts include any such salt known in the art. Where compounds of the present invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

As noted herein, the compounds of the present invention can be used in combination with other agents or other agents which will enhance the treatment regime for the mammalian subject. For example, the compounds of the methods could be used in combination with other estrogen receptor-β modulators. The individual components of such combinations can be administered separately at different times during the course of therapy or concurrently in divided or single combination forms to patients or regions of such patients in need of such therapy. The instant invention is therefore to be understood as embracing all such regimes of simultaneous or alternating treatment and the term "administering" is to be interpreted accordingly. It will be understood that the scope of combinations of the compounds of this invention with other agents useful to treat the targeted demyelinating disease includes in principle any combination with any pharmaceutical composition useful for treating disorders related to estrogen functioning.

The following non-limiting examples and data illustrate various aspects and features relating to the compounds, compositions and/or methods of the present invention, including the synthesis of 6-substituted estradiol derivatives, as are available though the methodologies described herein. In comparison with the prior art, the present compounds and methods provide results and data which are surprising, unexpected and contrary thereto. While the utility of this invention is illustrated through the preparation and use of several compounds, moieties and/or substituents thereof, it will be understood by those skilled in the art that comparable results are obtainable with various other compounds, moieties and/or substituents, as are commensurate with the scope of this invention.

As noted above, the compounds of the methods are prepared according the procedures disclosed in U.S. Ser. Nos. 12/627,874 and 13/232,798. To exemplify the synthetic schemes described above and in detail in U.S. Ser. No. 12/627,874, the preparation of compound 21 is provided in Example 1.

EXAMPLE 1

Methods for Preparing Compound 21 a) (8R,9S,13S,14S,17S)-3,17-bis(methoxymethoxy)-13-methyl-7,8,9,11,12,13,14,15,16,17-decahydro-6H-cyclopenta[a]phenanthrene—Chloromethyl methyl ether (7.0 mL, 92.0 mmol) is added to a solution of β-estradiol (5 g, 18.4 mmol) and diisopropylethylamine (16.0 mL 92 mmol) in 100 mL of THF. The reaction mixture is heated to reflux and stirred for 18 hours. The THF is removed in vacuo, and the yellow/brown oil is partitioned between water and $CH_2Cl_2$. The organic layer is separated, washed with brine, dried ($Na_2SO_4$), filtered, and evaporated in vacuo to give a golden oil. Purification by silica gel column chromatography (10% EtOAc/Hex) affords the title compound as a viscous, clear oil (5.7 g, 86%).

b) (8R,9S,13S,14S,17S)-3,17-bis(methoxymethoxy)-13-methyl-7,8,9,11,12,13,14,15,16,17-decahydro-6H-cyclopenta[a]phenanthren-6-ol—To a solution of potassium tert-butoxide (8.87 g, 79.0 mmol) and diisopropylamine (11.2 mL, 79.0 mmol) in 80 mL of anhydrous THF cooled to −78° C. under argon is added n-butyllithium (49.4 mL, 79.0 mmol, 1.6 M in hexane) dropwise. The reaction mixture is stirred at −78° C. for 30-45 minutes. A solution of the compound from a) (5.7 g, 15.8 mmol) in 45 mL of THF is then added dropwise, and the reaction mixture is stirred for 3 hours at −78° C. During the addition of the compound from a), the reaction turns a deep red color. Trimethyl borate (10.6 mL, 94.8 mmol) is then added slowly, and the mixture is warmed to 0° C. and stirred for 2 hours. Hydrogen peroxide (24 mL of a 30% aq. solution) is then added, and the reaction mixture is warmed to room temperature and stirred for a further 1 hour. The reaction is cooled back to 0° C. and carefully quenched with a 10% aq. $Na_2S_2O_3$ solution (70 ml). The resulting mixture is extracted with EtOAc (2×), and the combined organic extracts are dried ($Na_2SO_4$), filtered, and evaporated in vacuo to give a yellow/brown oil. Purification by silica gel column chromatography (25% EtOAc/Hex) affords the title compound as a white solid (3.5 g, 59%).

c) (8R,9S,13S,14S,17S)-3,17-bis(methoxymethoxy)-13-methyl-7,8,9,11,12,13,14,15,16,17-decahydro-6H-cyclopenta[a]phenanthren-6-one—Dess-Martin Periodinane (9.46 g, 22.3 mmol) is added portionwise to a solution of the compound from b) (7.0 g, 18.6 mmol) in 300 mL of $CH_2Cl_2$. The resulting reaction mixture stirred at room temperature for 3 hours. The mixture is poured into water and the layers are separated. The aqueous layer is extracted with $CH_2Cl_2$, and the combined organic extracts are washed with brine, dried ($Na_2SO_4$), filtered, and evaporated in vacuo to give a gooey, brown solid. Purification by silica gel column chromatography (15% EtOAc/Hex) affords the title compound as a pale yellow, viscous oil (6.0 g, 86%).

d) ethyl 2-(((8R,9S,13S,14S,17S)-3,17-bis(methoxymethoxy)-13-methyl-7,8,9,11,12,13,14,15,16,17-decahydro-6H-cyclopenta[a]phenanthren-6-ylidene)acetate—Triethyl phosphonoacetate (4.1 mL, 20.8 mmol) is added to a mixture of sodium hydride (832 mg, 20.8 mmol) in 25 mL of THF at room temperature. After approximately 10 minutes, a solution of the compound from c) (3.9 g, 10.4 mmol) in 10 mL of THF is added dropwise. The resulting reaction mixture is heated to reflux in a sealed tube for 72 hours. The mixture is concentrated in vacuo and purified by silica gel column chromatography (gradient from 5% EtOAc/Hex to 40% EtOAc/Hex) to give the title compound as a clear, viscous oil (3.4 g, 74%).

e) 2-((8R,9S,13S,14S,17S)-3,17-bis(methoxymethoxy)-13-methyl-7,8,9,11,12,13,14,15,16,17-decahydro-6H-cyclopenta[a]phenanthren-6-ylidene)ethanol—A solution of the compound from d) (3.1 g, 6.97 mmol) in 65 mL of THF is treated with lithium aluminum hydride (5.2 mL, 10.46 mmol, 2 M in THF) dropwise at 0° C. The cold bath is removed, and the reaction mixture is stirred at room temperature for 15 minutes. The reaction is cooled back to 0° C. and quenched by the careful addition of 1.3 mL of water, followed by 2.6 mL of 2N NaOH, and then 1.3 mL of water. The mixture is stirred vigorously until a white solid forms. The mixture is filtered, and the filtrate is concentrated in vacuo to give the title compound as a clear oil (2.8 g, 99%).

f) 2-((6S,8R,9S,13S,14S,17S)-3,17-bis(methoxymethoxy)-13-methyl-7,8,9,11,12,13,14,15,16,17-decahydro-6H-cyclopenta[a]phenanthren-6-yl)acetaldehyde—A mixture of the compound from e) (3.09 g, 7.68 mmol) and 10% Pd/C (500 mg) in 100 mL of ethyl acetate is stirred under 40 psi of $H_2$ (g) for 5 hours at room temperature. The mixture is filtered through Celite, and the Celite is washed well with ethyl acetate. The filtrate is concentrated in vacuo to give a pale yellow oil (3.1 g). The oil is dissolved in 100 mL of dichloromethane, and Dess-Martin Periodinane (3.9 g, 9.22 mmol) is added portionwise. The resulting reaction mixture is stirred at room temperature for 30 minutes. The mixture is poured into water and extracted with $CH_2Cl_2$. The combined organic extracts are washed with brine, dried ($Na_2SO_4$), filtered, and evaporated in vacuo to give a brown solid. Purification by silica gel column chromatography (15% EtOAc/Hex) affords the title compound as a clear oil (2.0 g, 65%).

g) 4-((6R,8R,9S,13S,14S,17S)-3,17-bis(methoxymethoxy)-13-methyl-7,8,9,11,12,13,14,15,16,17-decahydro-6H-cyclopenta[a]phenanthren-6-yl)but-2-en-1-ol—Lithium bis(trimethylsilyl)amide (18.4 mL, 18.4 mmol, 1.0 M in THF) is added dropwise to a suspension of (2-hydroxyethyl) triphenylphosphonium bromide (3.37 g, 8.70 mmol) in 60 mL of THF at 0° C. After 1 hour, the golden brown solution is treated with a solution of the compound from f) (1.4 g, 3.48 mmol) in 10 mL of THF dropwise. The resulting reaction mixture is stirred at 0° C. for 40 minutes and then quenched with saturated aqueous $NH_4Cl$. The resulting mixture is extracted with EtOAc (2×), and the combined organic extracts are dried ($Na_2SO_4$), filtered, and evaporated to give a brown oil. Purification by silica gel column chromatography (gradient from 20% EtOAc/Hex to 75% EtOAc/Hex) affords the title compound as a yellow, viscous oil (680 mg, 45%).

h) 4-((6R,8R,9S,13S,14S,17S)-3,17-bis(methoxymethoxy)-13-methyl-7,8,9,11,12,13,14,15,16,17-decahydro-6H-cyclopenta[a]phenanthren-6-yl)but-2-enal—Dess-Martin Periodinane (437 mg, 1.03 mmol) is added to a solution of the compound from g) (370 mg, 0.86 mmol) in 15 mL of $CH_2Cl_2$ at room temperature. The resulting reaction mixture is stirred for 10 minutes and then poured into water. The layers are separated and the aqueous layer is extracted with $CH_2Cl_2$ (2×). The combined organic extracts are washed with brine, dried ($Na_2SO_4$), filtered, and evaporated in vacuo to give a brown oil. Purification by silica gel column chromatography (gradient from 5% EtOAc/CH2Cl2 to 10% EtOAc/$CH_2Cl_2$) affords the title compound as a pale yellow, viscous oil (358 mg, 86%).

i) 6-((6R,8R,9S,13S,14S,17S)-3,17-bis(methoxymethoxy)-13-methyl-7,8,9,11,12,13,14,15,16,17-decahydro-6H-cyclopenta[a]phenanthren-6-yl)hexa-2,4-dien-1-ol—Lithium bis(trimethylsilyl)amide (4.3 mL, 4.29 mmol, 1.0 M in THF) is added dropwise to a suspension of (2-hydroxyethyl) triphenylphosphonium bromide (786 mg, 2.03 mmol) in 14 mL of THF at 0° C. After 30 minutes, the golden brown solution is treated with a solution of the compound from h) (345 mg, 0.81 mmol) in 2 mL of THF dropwise. The resulting reaction mixture is stirred at 0° C. for 20 minutes and quenched with saturated aqueous $NH_4Cl$. The resulting mixture is extracted with EtOAc (2×), and the combined organic extracts are dried ($Na_2SO_4$), filtered, and evaporated to give a brown oil. Purification by silica gel column chromatography (gradient from 5% EtOAc/$CH_2Cl_2$ to 40% EtOAc/$CH_2Cl_2$) affords the title compound as a yellow, viscous oil (140 mg, 38%).

j) (6R,8R,9S,13S,14S,17S)-6-(6-methoxyhexa-2,4-dien-1-yl)-3,17-bis(methoxymethoxy)-13-methyl-7,8,9,11,12,13,14,15,16,17-decahydro-6H-cyclopenta[a]phenanthrene—A solution of the compound in i) (135 mg, 0.3 mmol) is cooled to 0° C., and sodium hydride (120 mg, 3.0 mmol) is added portionwise. After 5-10 minutes, iodomethane (0.19 mL, 3.0 mmol) is added dropwise, and the resulting reaction mixture is warmed to room temperature and stirred for 4 hours. EtOAc is added and the reaction is carefully quenched with water. The layers are separated and the organic layer is dried ($Na_2SO_4$), filtered, and evaporated to give a brown oily residue. Purification by silica gel column chromatography (gradient from 5% EtOAc/Hex to 20% EtOAc/Hex) affords the title compound as a clear oil (92 mg, 65%).

k) (6R,8R,9S,13S,14S,17S)-6-(6-methoxyhexyl)-3,17-bis(methoxymethoxy)-13-methyl-7,8,9,11,12,13,14,15,16,17-decahydro-6H-cyclopenta[a]phenanthrene—A mixture of the compound in j) (90 mg, 0.19 mmol) and 10% Pd/C (100 mg) in 5-10 mL of ethyl acetate is stirred under a balloon of $H_2$ (g) for 16 hours at room temperature. The mixture is filtered through Celite, and the Celite is washed well with ethyl acetate. The filtrate is concentrated in vacuo to give the title compound as a clear oil (90 mg, 99%).

l) (6R,8R,9S,13S,14S)-6-(6-methoxyhexyl)-13-methyl-7,8,9,11,12,13,14,15,16,17-decahydro-6H-cyclopenta[a]phenanthrene-3,17-diol (Compound 21)—A solution of the compound from k) (90 mg, 0.19 mmol) in 1.5 mL each of 6 N HCl and THF is stirred for 5 hours at room temperature. The reaction mixture is diluted with water and extracted with EtOAc (2×). The combined organic extracts are dried ($Na_2SO_4$), filtered, and evaporated in vacuo to give a clear, oily residue. Purification by silica gel column chromatography (gradient from CH2Cl2 to 30% EtOAc/CH2Cl2) afforded Compound 21 as a white solid foam (38 mg, 52%).

EXAMPLE 2

Methods for Preparing Compounds 3 and 4

As outlined in Scheme 2, estradiol derivatives compounds 3 and 4 are synthesized in the following manner. The protected estradiol compound is prepared by reaction of β-estradiol with dihydropyran in THF, using toluenesulfonic acid or camphorsulfonic acid as catalyst. As one of ordinary skill in the art can appreciate, this reaction is an equilibrium reaction and does not go to completion under such conditions. Thus, both the mono-protected estradiols can be found in the reaction mixture. Such crude reaction mixture undergoes a trituration step with acetonitrile causing the desired bis-THP estradiol to crystallize in approximately 70% yield.

As shown in Scheme 2, the key intermediate is obtained via acylation at the benzylic 6-position with the strong base mixture referred to as LiDAKOR: butyl lithium, diisopropylamine, and potassium tert-amylate. Under such conditions at −70° C., one of ordinary skill in the art can appreciate the abstraction of a proton at a benzylic position. The intermediate is then purified by column chromatography to give a syrup in approximately 50% yield, still containing minor impurities and column solvents. Reduction of the aldehyde with an excess of lithium aluminum hydride results in high yields of the racemic hydroxymethyl estradiol compound.

For purposes of preparing compounds 3 and 4, the methoxymethyl compound is prepared by methylation of hydroxymethyl estradiol compound with sodium hydride and methyl iodide. The methoxymethyl compound is purified by column chromatography to give a glassy foam. Deprotecting the protected groups give racemic 6-methoxymethyl estradiol compound. Separation of the enantiomers is performed using chiral preparative HPLC to give the compounds 3 and 4. For compound 4, a chiral purity of >95:5 R:S is realized. For compound 3, a chiral purity of 86:14 S:R is realized. It is well within the level of one of ordinary skill in the art to employ NMR for determination of the absolute stereochemistry of the 6-position, where the 4- and 6-protons are diagnostic.

EXAMPLE 3

Expression Profiling of Compounds in Lung, Pancreas, and Ovarian Tumor Cell Lines The study includes three human tumor cell lines: A549, Panc-1, and SK-OV-3. The lines are each grown in two flasks cultured to roughly 40% confluence. One of the flasks is treated by addition of compound to the culture media at a various concentrations, i.e. 10 µM, 20 µM 50 µM, 100 µM or 200 µM. The other, mock treated, flask is treated only with the vehicle used to solubilize and deliver the drug. RNA extracted from the pairs of treated and untreated samples is subjected to microarray analysis on Agilent Whole Human Genome Microarrays (G4112F). Each analysis reports the difference in abundance of messenger RNAs for each of the 41,000 specific mRNA detectors on the array. This direct comparison of the treated versus untreated samples for each cell line provides extremely sensitive detection of changes in mRNA abundance resulting from the drug treatment. As each cell line comparison is self-normalized, the results can be compared across the samples with high confidence.

Cell Preparation

Three human tumor cell lines, A549, Panc-1, and SK-OV-3, are each grown in two flasks cultured to roughly 40% confluence. One of the flasks is treated by addition of compound to the culture media at concentrations of 10 µM, 50 µM and 100 µM. The other, mock treated, flask is treated only with the vehicle used to solubilize and deliver the drug. All flasks are cultured for a further 24 hours, and then the cells are scraped free and washed in ice-cold PBS, then collected by centrifugation. The harvested cells are immediately frozen, and stored at −80° C. or colder.

RNA Purification

Total RNA is prepared from the frozen tissue samples using Trizol-based cell lysis followed by 65° C. hot phenol extraction and RNeasy chromatography purification. The purified RNA samples are analyzed spectrophotometrically. The concentration of RNA is determined by measuring the absorbance at 260 nm (A260). Given an absorbance of 1 unit at 260 nm corresponds to 35 µg of RNA per ml when measured at pH 11.

RNA Quality Assessment—A260/A280 Absorbance Ratios

The ratio of the readings at 260 nm and 280 nm (A260/A280) provides an estimate of the purity of RNA with respect to contaminants that absorb UV, such as protein. RNA has a theoretical A260/A280 ratio (10 mM Tris.Cl, pH 7.5) of approximately 2.1. Extracted RNAs having an A260/A280 ratio of 1.8 or greater provide excellent results in this assay.

RNA Quality Assessment—Capillary Electrophoresis

The RNA is tested for relative integrity by determining the ratio of intact 28S and 18S ribosomal RNAs, using capillary electrophoresis (Agilent BioAnalyzer). Completely intact RNA has a 28S/18S ratio of 2.2. All RNAs accepted for array analysis have ratios exceeding 1, the minimal 28S/18S ratio for reliably reproducible microarray results as determined by review of internal reproducibility among samples with varying 28S/18S ratios.

Probe Production and Chip Hybridization

All RNAs are labeled using 1 microgram of RNA as input to an Agilent Low Input Labeling reaction.

Test RNA is labeled with Cy5 (650 nm emitter) and reference RNA is labeled with Cy3 (550 nm emitter) nucleotides. Labeling, hybridizations and subsequent washings are carried out on Agilent H1Av2 human expression chips. The resulting hybridized chips are scanned on an Agilent microarray scanner, and intensity information for each detector spot is extracted from the scanned image using Agilent feature extraction software.

The most telling test of the quality of the hybridization is the level of variance in reported ratios from the large number of duplicates of genes printed on these chips. A set of gene probes is each printed ten times in random positions across the array. The median value of the standard deviation of the $\log_2$ ratio across all the sets is used as an estimator of the overall standard deviation across the entire array.

Data and Analysis

The key data for all three hybridizations is collected in a FileMaker Pro relational database to allow for easy formulation of searches that can identify genes that exhibit particular transcriptional patterns. The data reported are the red (treated) and green (untreated) background-subtracted signals. This is the least modified form of the data. A background "surface" is estimated across the slide, based on numerous probes that are not complementary to human DNA. These serve as estimators of both non-specific binding of labeled cRNA to array surfaces and non-specific binding of labeled cRNA to the immobilized DNA oligomers. Using this information, local noise around each probe is estimated and this is subtracted from the signal found at the area of oligonucleotide deposition for each particular probe feature on the array (gBGSub Signal, rBGSub Signal). The ratio of signal from the RNA of the treated cell and the RNA of the untreated cell is reported both as a direct ratio and as the $\log_2$ ratio (Ratio, Log 2Ratio). Ratios are determined in an iterative process that normalizes the intensities in each channel, so that a scalar is found that maximizes the similarity of intensities of the large number of genes that have nearly identical transcriptional levels, and thus should have ratios very close to 1.

After the ratios have been calculated for the normalized data, the various control and duplicate samples are analyzed to build a model of how reproducible the results are, and how this reproducibility is varies depending on signal strength and noise. With these parameters, an estimate of the likelihood that each ratio could have arisen if the red and green intensities are randomly drawn from a single process that produced the same distribution of intensities is produced. This probability is reported for each sample and is a measure of the probability that the ratio indicates a difference between the treated and untreated signal strengths (PValLogRatio). This probability can be used to threshold the results into changed and unchanged genes. In the database, a threshold of p≤0.001 is used as the cut point for significant change in mRNA abundance between the treated and untreated sample (Sig0.001). This threshold reduces the number of expected false positives to a reasonable level given the ~40,000 ratios that are being surveyed in each assay. A field that indicates significant change and the direction of the change relative to the untreated sample reduces the result of the assay to a trinary categorical; 1, up regulated relative to untreated, 0, unchanged relative to untreated and −1, down regulated relative to untreated (Tri). Using this representation, one easily constructs searches that identify genes that have changed in any single or multiple sets of experiments.

The gene expression data found in Table 1 below shows that compound 4 and compound 21 up-regulate genes in signaling pathways involved in proliferation and differentiation of OPCs, and ultimately the synthesis of myelin sheaths at nerve axons. Gene expression values shown in Table 1 are $\log_2$ values and an average of data obtained from three human tumor cell lines (SKOV-3, A549 and Panc-1). A significant change in gene expression is p≤0.0001. Gene IDs conform to standards developed at the National Center for Biotechnology Information (NCBI) for the Entrez Gene database.

from passage 2 are used to prepare two 96-well plates for the primary screen. Following the initial 48 hour incubation in OPC media, the OPCs are treated with 10 μM of 17β-estradiol, compound 4 and compound 21, along with vehicle control DMSO and positive control compounds including 10 μM ciliary neurotrophic factor (CNTF) and 1 μM extracellular-signal-regulated (ERK) kinase inhibitor (MEKi). Cells are treated for a total of 4 days and the media is replaced once at the 48 hour mark with fresh compounds. After the 4 day treatment the cells are fixed with 4% paraformaldehyde and stained with Hoechst 33342 to visualize nuclei. Cells are also stained with anti-GFAP (GFAP=glial fibrillary acidic protein) antibodies to identify astrocytes. Cells are blocked with 3% normal goat serum followed by an overnight incubation of anti-rabbit GFAP antibody (1:500). Cells are labeled with a 1:1000 concentration of secondary goat anti-rabbit Alexa 647 fluorochrome antibody. Images are acquired using the Cellomics Arrayscan VTI. Twenty fields at 10× magnification are acquired per well and the cells expressing EGFP (enhanced green gluorescent protein; mature oligodendrocytes) and GFAP (astrocytes) are evaluated by neuronal profiling algorithm.

Figure 2:
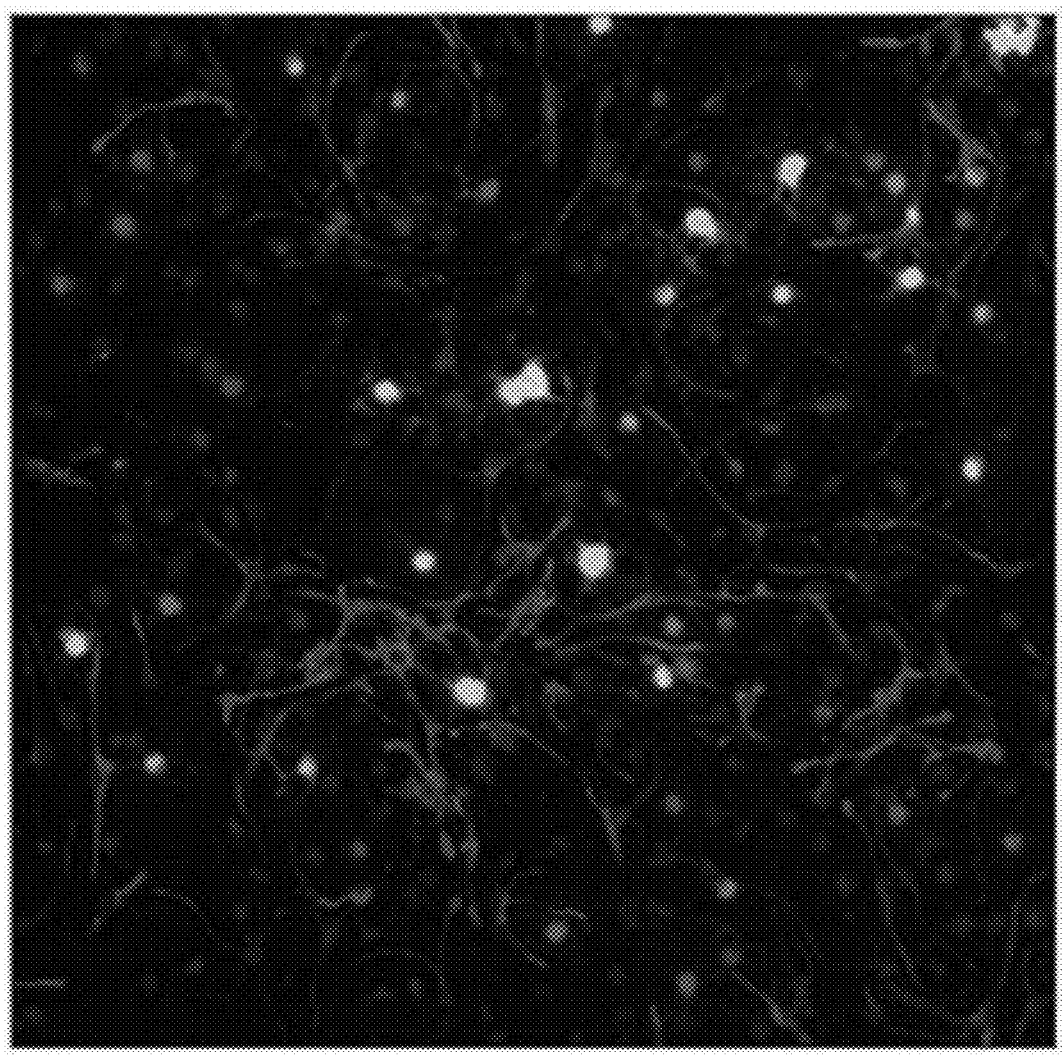
FIG. 2 depicts oligodendrocyte maturation in mouse culture after 96 hours of treatment with 10 μM of compound 21; a) treatment with negative control (DMSO); b) treatment with positive control (MEKi); c) treatment with compound 21.
Figure 3:
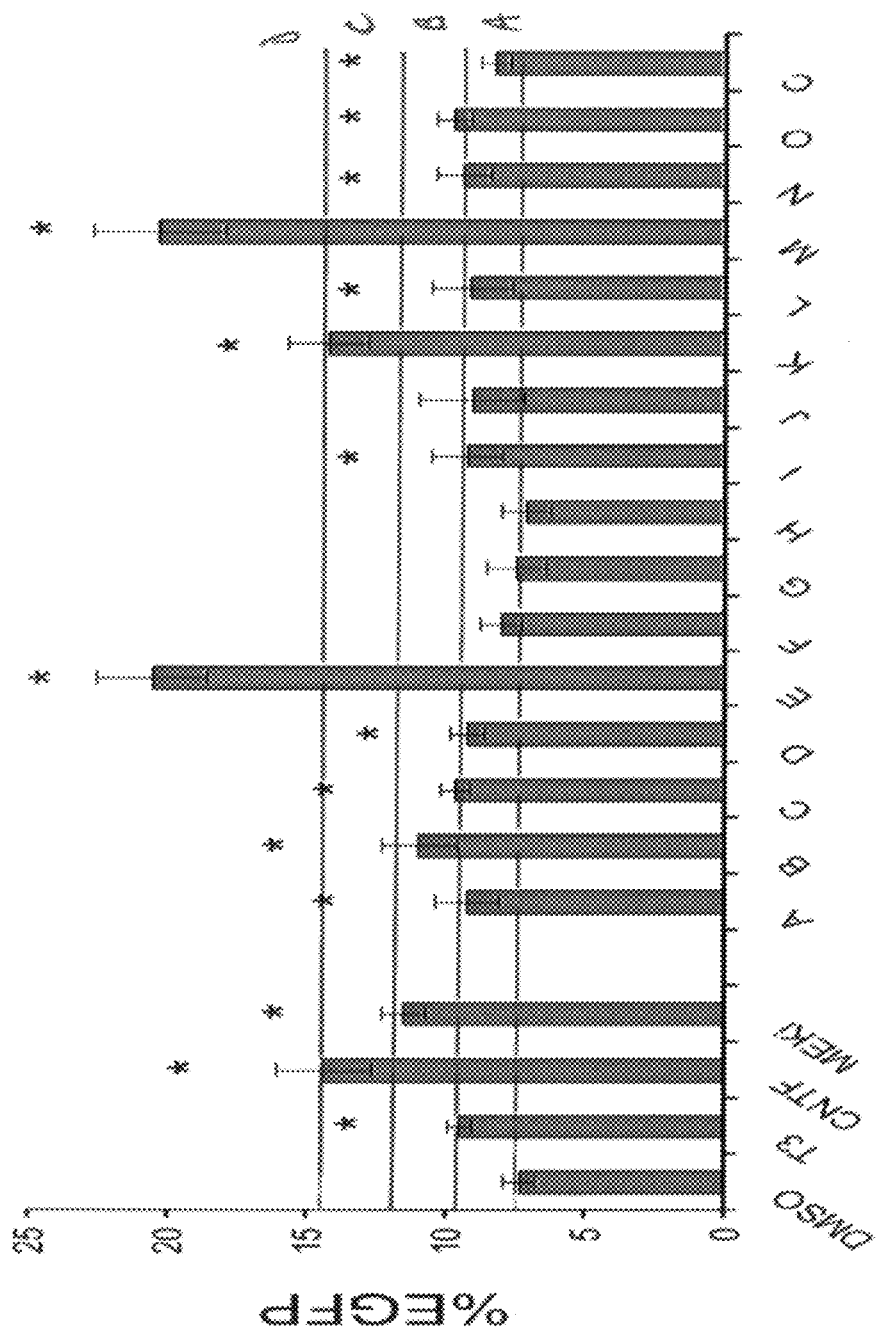
FIG. 3 gives a comparison of the ability of various 6-substituted estradiol derivatives to differentiate OPCs into mature oligodendrocytes, to the ability of control drugs T3, CNTF and MEKi to differentiate OPCs into mature oligodendrocytes.
Figure 4:
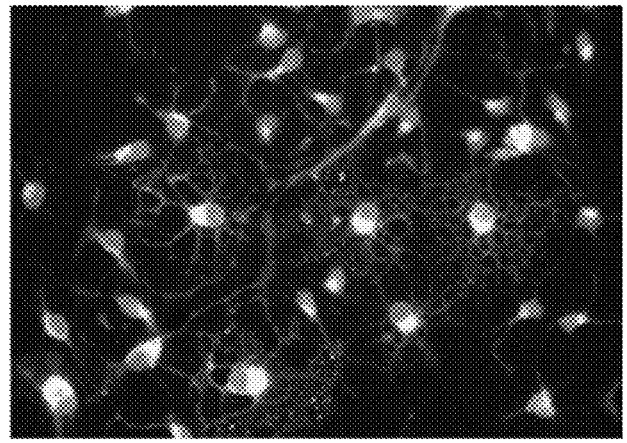
FIG. 4 depicts process extensions representative of oligodendrocytes after treatment with compound 8.

The extent of oligodendrocyte maturation is measured by the level of the PLP-EGFP reporter signal, along with the extent of process formation (FIGS. 1-4; legend for FIGS. 1 and 3 are presented below in Table 2). Proteolipid protein (PLP) is used as a biomarker because it is known to be expressed in mature oligodendrocytes and is a component of the myelin sheath. As shown in FIGS. 1 and 3, both compound 4 and 21 are potent 6-substituted analogs, with compound 21 having 3-fold more activity to differentiate oligodendrocytes compared to DMSO and 1.5 to 2.0-fold more activity than the positive controls CNTF (Stankoff, B. et al., *J Neurosci* 22(21), 9221-27 (2002)) and MEKi Younes-Rapozo, V. et al., *Int J Dev Neurosci*, 27(8), 757-68 (2009)), respectively. Compared to DMSO and all other compounds tested, including CNTF, the extent of process formation is also greatest for compound 21 (FIGS. 2 and 4).

TABLE 1

| Gene | Symbol | Entrez Gene Database ID | Cmpd 4 (50 μM) | Cmpd 4 (100 μM) | Cmpd 21 (10 μM) | Cmpd 21 (50 μM) |
| --- | --- | --- | --- | --- | --- | --- |
| Delta/notch-like EFG repeat | DNER | 92737 | 5.16 | 5.51 | 6.20 | 4.79 |
| Oligodentrocyte lineage transcription factor 2 | OLIG2 | 10215 | 4.98 | 4.59 | 6.16 | 5.32 |
| Myelin basic protein (variant 7) | MBP | 4155 | 4.72 | 4.80 | 6.07 | 5.04 |
| Myelin oligodentrocyte glycoprotein (variant alpha 4) | MOG | 4340 | 3.99 | 4.28 | 5.23 | 5.55 |
| Interleukin 23 receptor | IL23R | 149233 | 3.62 | 4.86 | 5.31 | 5.46 |
| Transmembrane protein 108 | TMEM108 | 66000 | 3.59 | 3.62 | 3.92 | 3.96 |
| Connexin | AF251047 | 100128922 | 3.38 | 3.56 | 2.74 | 3.08 |
| Interleukin 20 receptor alpha | IL20RA | 53832 | 3.17 | 3.38 | 4.42 | 4.39 |
| Interleukin 28A | IL28A | 282616 | 1.35 | 1.96 | 1.44 | 2.59 |

EXAMPLE 4

Oligodendrocyte Differentiation Assay

OPC cultures are prepared as described Pedraza, C. E. et al., *Glia* 56(12), 1339-52 (2008), incorporated herein by reference. Brains are removed from E14.5 C57B16/J (expressing PLP-EGFP) mice (Mallon, B. S. et al., *J. Neurosci* 22(3), 876-85 (2002)), cleaned and cortical hemispheres are isolated. Tissue is then triturated and seeded in T-25 cm$^2$ flasks at a density of 1 brain (2 cortical hemispheres) per flask. Neurospheres are passaged once after 3 days. Cells

TABLE 2

| Legend for FIGS. 1 and 3 | |
| --- | --- |
| Letter in FIGS. 1 and 3 | Compound # |
| A | 24 |
| B, O | 4 |
| C | 8 |
| D | Estradiol |
| E, M | 21 |
| F | 32 |

TABLE 2-continued

Legend for FIGS. 1 and 3

| Letter in FIGS. 1 and 3 | Compound # |
|---|---|
| G | 23 |
| H | Estriol |
| I | 10 |
| J | 18 |
| K | 20 |
| L | Exemestane |
| N | 33 |

The disclosures of all articles and references, including patents, are incorporated herein by reference. The invention and the manner and process of making and using it are now described in such full, clear, concise and exact terms as to enable any person skilled in the art to which it pertains, to make and use the same. All references cited in this specification are incorporated herein by reference. It is to be understood that the foregoing describes preferred embodiments of the present invention and that modifications may be made therein without departing from the spirit or scope of the present invention.

What is claimed is:

1. A method of treating demyelination and/or enhancing remyelination of an axon of a nerve cell that is in need of remyelination, comprising:
providing a compound of a formula:

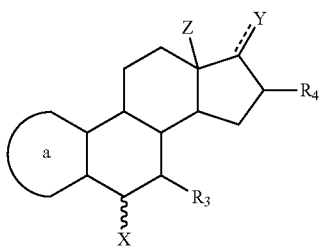

wherein the "a" ring is

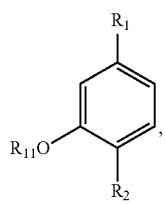

$R_1$, $R_2$, $R_3$ and $R_4$ are independently selected from the group consisting of H, $C_1$-$C_6$ alkyl, halo, a sulfate, a glucuronide, and —OH;
$R_{11}$ is selected from the group consisting of H, $C_1$-$C_6$ alkyl, a sulfate, a glucoronide, —$SO_2NH_2$, —$OSO_2$alkyl, and —$NH_2$;
X is selected from the group consisting of $C_1$-$C_{12}$ alkyl, $C_2$-$C_{12}$ alkenyl, —SH, —$SCH_3$, —$(CH_2)_m$—O—$CH_3$, —$(CH_2)_m$—O—$(CH_2)_n$$CH_3$, $(CH_2)_m$—S—$CH_3$, —$(CH_2)_m$—S—$(CH_2)_n$$CH_3$, —$(CH_2)_m$—NH—$(CH_2)_n$$CH_3$, —$C_2$-$C_8$ alkenyl-O—$(CH_2)_n$$CH_3$, —$C_2$-$C_8$ alkenyl-S—$(CH_2)_n$$CH_3$, —$C_2$-$C_8$ alkenyl-NH—$(CH_2)_n$$CH_3$, —$(CH_2)_m$—OH, —$(CH_2)_m$—$NH_2$, —$(CH_2)_m$—O—$NH_2$, —$(CH_2)_m$—S—$NH_2$, —$NH(CH_2)_m$$CH_3$, —$NH(CH_2)_m$$OCH_3$, —$N(CH_3)_2$, —$(CH_2)_m$(NH)$CH_2OH$, and —$(CH_2)_m$ $N(CH_3)$—$SO_2$—$NH_3$;
Y is selected from the group consisting of OH, and =O;
Z is selected from the group consisting of H and methyl;
m is an integer selected from 0-20;
n is an integer selected from 0-8;
the ---- symbol represents either a single or a double bond capable of forming a keto group at position 17; and
the ∿∿∿ symbol represents any type of bond regardless of the stereochemistry; and the respective enantiomers, other stereochemical isomers, tautomers and pharmaceutically acceptable salts of said compounds; and
contacting one or more progenitor cells with an effective amount of a said compound to differentiate the one or more progenitor cells to one or more cells that form myelin, thereby enhancing remyelination of the axon of a nerve cell.

2. A method according to claim 1 wherein
Y is —OH;
Z is methyl;
$R_{11}$ is H;
$R_4$ is selected from the group consisting of H, halo and $C_1$-$C_6$ alkyl;
$R_1$ and $R_2$ are independently selected from the group consisting of H, —OH and halo;
$R_3$ is selected from the group consisting of H, halo and —OH;
m is an integer from 1-12; and
n is an integer from 0-4.

3. A method according to claim 2 wherein
X is selected from the group consisting of $C_1$-$C_{12}$ alkyl, $C_2$-$C_{12}$ alkenyl, —$(CH_2)_m$—O—$CH_3$, —$(CH_2)_m$—O—$(CH_2)_n$$CH_3$, $(CH_2)_m$—S—$CH_3$, and —$(CH_2)_m$—S—$(CH_2)_n$$CH_3$.

4. A method according to claim 1 wherein the compound is selected from the group consisting of
(6S,8R,9S,13S,14S)-3-hydroxy-6-(methoxymethyl)-13-methyl-7,8,9,11,12,13,15,16-octahydro-6H-cyclopenta[a]phenanthren-17(14H)-one;
(6R,8R,9S,13S,14S)-3-hydroxy-6-(methoxymethyl)-13-methyl-7,8,9,11,12,13,15,16-octahydro-6H-cyclopenta[a]phenanthren-17(14H)-one;
(6S,8R,9S,13S,14S)-6-(methoxymethyl)-13-methyl-7,8,9,11,12,13,14,15,16,17-decahydro-6H-cyclopenta[a]phenanthrene-3,17-diol;
(6R,8R,9S,13S,14S)-6-(methoxymethyl)-13-methyl-7,8,9,11,12,13,14,15,16,17-decahydro-6H-cyclopenta[a]phenanthrene-3,17-diol; (6S,8R,9S,10R,13S,14S)-17-hydroxy-6-(methoxymethyl)-10,13-dimethyl-6,7,8,9,10,11,12,13,14,15,16,17-dodecahydro-3H-cyclopenta[a]phenanthren-3-one;
(6R,8R,9S,10R,13S,14S)-17-hydroxy-6-(methoxymethyl)-10,13-dimethyl-6,7,8,9,10,11,12,13,14,15,16,17-dodecahydro-3H-cyclopenta[a]phenanthren-3-one;
(6S,8R,9S,13S,14S)-6-(hydroxymethyl)-13-methyl-7,8,9,11,12,13,14,15,16,17-decahydro-6H-cyclopenta[a]phenanthrene-3,17-diol;
(6R,8R,9S,13S,14S)-6-(hydroxymethyl)-13-methyl-7,8,9,11,12,13,14,15,16,17-decahydro-6H-cyclopenta[a]phenanthrene-3,17-diol;
(6R,8R,9S,10R,13S,14S)-6-(methoxymethyl)-10,13-dimethylhexadecahydro-1H-cyclopenta[a]phenanthrene-3,17-diol;

(6R,8R,9S,13S,14S)-6-((aminooxy)methyl)-13-methyl-7,8,9,11,12,13,14,15,16,17-decahydro-6H-cyclopenta[a]phenanthrene-3,17-diol;

(6S,8R,9S,13S,14S)-6-((aminooxy)methyl)-13-methyl-7,8,9,11,12,13,14,15,16,17-decahydro-6H-cyclopenta[a]phenanthrene-3,17-diol;

(6R,8R,9S,13S,14S)-6-((aminooxy)methyl)-17-hydroxy-13-methyl-6,7,8,9,10,11,12,13,14,15,16,17-dodecahydro-3H-cyclopenta[a]phenanthren-3-one;

(6S,8R,9S,13S,14S)-6-((aminooxy)methyl)-17-hydroxy-13-methyl-6,7,8,9,10,11,12,13,14,15,16,17-dodecahydro-3H-cyclopenta[a]phenanthren-3-one;

(6R,8R,9S,13S,14S)-6-(((methoxymethyl)amino)methyl)-13-methyl-7,8,9,11,12,13,14,15,16,17-decahydro-6H-cyclopenta[a]phenanthrene-3,17-diol;

(6S,8R,9S,13S,14S)-6-(((methoxymethyl)amino)methyl)-13-methyl-7,8,9,11,12,13,14,15,16,17-decahydro-6H-cyclopenta[a]phenanthrene-3,17-diol;

1-(((((6R,8R,9S,13S,14S)-3,17-dihydroxy-13-methyl-7,8,9,11,12,13,14,15,16,17-decahydro-6H-cyclopenta[a]phenanthren-6-yl)methyl)amino)propan-2-one;

1-(((((6S,8R,9S,13S,14S)-3,17-dihydroxy-13methyl-7,8,9,11,12,13,14,15,16,17-decahydro-6H-cyclopenta[a]phenanthren-6-yl)methyl)amino)propan-2-one;

(6R,8R,9S,13S,14S)-6-methoxy-13-methyl-7,8,9,11,12,13,14,15,16,17-decahydro-6H-cyclopenta[a]phenanthrene-3,17-diol;

(6S,8R,9S,13S,14S)-6-(2-methoxyethyl)-13-methyl-7,8,9,11,12,13,14,15,16,17-decahydro-6H-cyclopenta[a]phenanthrene-3,17-diol;

(6R,8R,9S,13S,14S)-6-(4-methoxybutyl)-13-methyl-7,8,9,11,12,13,14,15,16,17-decahydro-6H-cyclopenta[a]phenanthrene-3,17-diol;

(6R,8R,9S,13S,14S)-6-(6-methoxyhexyl)-13-methyl-7,8,9,11,12,13,14,15,16,17-decahydro-6H-cyclopenta[a]phenanthrene-3,17-diol;

(6R,8R,9S,13S,14S)-6-(6-methoxyoctyl)-13-methyl-7,8,9,11,12,13,14,15,16,17-decahydro-6H-cyclopenta[a]phenanthrene-3,17-diol;

(6R,8R,9S,13S,14S)-3-hydroxy-6-(methoxymethyl)-13-methyl-7,8,9,11,12,13,14,15,16,17-decahydro-6H-cyclopenta[a]phenanthren-17-yl stearate;

(6R,8R,9S,10R,13S,14S)-6-(methoxymethyl)-10,13-dimethyl-7,8,9,10,11,12,13,14,15,16-decahydro-3H-cyclopenta[a]phenanthrene-3,17(6H)-dione;

(6S,8R,9S,10R,13S,14S)-6-(methoxymethyl)-10,13-dimethyl-7,8,9,10,11,12,13,14,15,16-decahydro-3H-cyclopenta[a]phenanthrene-3,17(6H)-dione;

(6R,8R,9S,10R,13S,14S)-6-(methoxymethyl)-10,13-dimethyl-4,5,6,7,8,9,10,11,12,13,14,15,16,17-tetradecahydro-3H-cyclopenta[a]phenanthrene-3,17-diol;

(6S,8R,9S,10R,13S,14S)-6-(methoxymethyl)-10,13-dimethyl-4,5,6,7,8,9,10,11,12,13,14,15,16,17-tetradecahydro-3H-cyclopenta[a]phenanthrene-3,17-diol;

(6S,8R,9S,13S,14S)-6-(methoxymethyl)-13-methyl-17-oxo-7,8,9,11,12,13,14,15,16,17-decahydro-6H-cyclopenta[a]phenanthren-3-yl hydrogen sulfate;

(6R,8R,9S,13S,14S)-6-(methoxymethyl)-13-methyl-17-oxo-7,8,9,11,12,13,14,15,16,17-decahydro-6H-cyclopenta[a]phenanthren-3-yl hydrogen sulfate;

(6R,8R,9S,13S,14S)-13-methyl-6-(4-propoxybutyl)-7,8,9,11,12,13,14,15,16,17-decahydro-6H-cyclopenta[a]phenanthrene-3,17-diol;

(6R,8R,9S,13S,14S)-13-methyl-6-(5-ethoxypentyl)-7,8,9,11,12,13,14,15,16,17-decahydro-6H-cyclopenta[a]phenanthrene-3,17-diol;

(6R,8R,9S,10R,13S,14S)-6-(methoxymethyl)-10,13-dimethylhexadecahydro-1H-cyclopenta[a]phenanthrene-3,17-diol; and (6R,8S,9S,14S,17S)-6-(methoxymethyl)-7,8,9,11,12,13,14,15,16,17-decahydro-6H-cyclopenta[a]phenanthrene-3,17-diol.

5. A method according to claim 4 wherein the compound is selected from the group consisting of (6R,8R,9S,13S,14S)-6-(methoxymethyl)-13-methyl-7,8,9,11,12,13,14,15,16,17-decahydro-6H-cyclopenta[a]phenanthrene-3,17-diol and (6R,8R,9S,13S,14S)-6-(6-methoxyhexyl)-13-methyl-7,8,9,11,12,13,14,15,16,17-decahydro-6H-cyclopenta[a]phenanthrene-3,17-diol.

6. A method of treating a demyelinating disorder in a subject, the method comprising:
(i) administering to the subject an effective amount of a 6-substituted estradiol derivative of the formula:

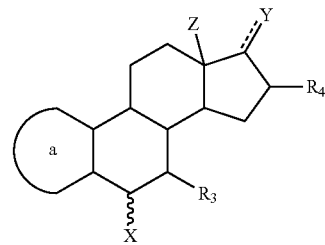

wherein the "a" ring is

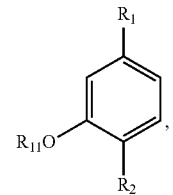

$R_1$, $R_2$, $R_3$ and $R_4$ are independently selected from the group consisting of H, $C_1$-$C_6$ alkyl, halo, a sulfate, a glucuronide, and —OH;

$R_{11}$ is selected from the group consisting of H, $C_1$-$C_6$ alkyl, a sulfate, a glucoronide, —$SO_2NH_2$, —$OSO_2$alkyl, and —$NH_2$;

X is selected from the group consisting of $C_1$-$C_{12}$ alkyl, $C_2$-$C_{12}$ alkenyl, —SH, —$SCH_3$, —$(CH_2)_m$—O—$CH_3$, —$(CH_2)_m$—O—$(CH_2)_n CH_3$, —$(CH_2)_m$—S—$CH_3$, —$(CH_2)_m$—S—$(CH_2)_n CH_3$, —$(CH_2)_m$—NH—$(CH_2)_n CH_3$, —$C_2$-$C_8$ alkenyl—O—$(CH_2)_n CH_3$, —$C_2$-$C_8$ alkenyl—S—$(CH_2)_n CH_3$, —$C_2$-$C_8$ alkenyl-NH—$(CH_2)_n CH_3$, —$(CH_2)_m$—OH, —$(CH_2)_m$—$NH_2$, —$(CH_2)_m$—O—$NH_2$, —$(CH_2)_m$—S—$NH_2$, —$NH(CH_2)_m CH_3$, —$NH(CH_2)_m OCH_3$, —$N(CH_3)_2$, —$(CH_2)_m(NH)CH_2OH$, and —$(CH_2)_m N(CH_3)$—$SO_2$—$NH_3$;

Y is selected from the group consisting of OH, and =O;

Z is selected from the group consisting of H and methyl;

m is an integer selected from 0-20;

n is an integer selected from 0-8;

the ---- symbol represents either a single or a double bond capable of forming a keto group at position 17; and the ∾∾∾ symbol represents any type of bond regardless of the stereochemistry; and the respective enantiomers, other stereochemical isomers, tautomers and pharmaceutically acceptable salts of said compounds; and
(ii) monitoring the subject for remyelination.

7. A method according to claim 6 wherein
Y is —OH;
Z is methyl;
$R_{11}$ is H;
$R_4$ is selected from the group consisting of H, halo and $C_1$-$C_6$ alkyl;
$R_1$ and $R_2$ are independently selected from the group consisting of H, —OH and halo;
$R_3$ is selected from the group consisting of H, halo and —OH;
m is an integer from 1-12; and
n is an integer from 0-4.

8. A method according to claim 7 wherein
X is selected from the group consisting of $C_1$-$C_{12}$ alkyl, $C_2$-$C_{12}$ alkenyl, —$(CH_2)_m$—O—$CH_3$, —$(CH_2)_m$—O—$(CH_2)_n CH_3$, $(CH_2)_m$—S—$CH_3$, and —$(CH_2)_m$—S—$(CH_2)_n CH_3$.

9. A method according to claim 6 wherein the compound is selected from the group consisting of
(6S,8R,9S,13S,14S)-3-hydroxy-6-(methoxymethyl)-13-methyl-7,8,9,11,12,13,15,16-octahydro-6H-cyclopenta[a]phenanthren-17(14H)-one;
(6R,8R,9S,13S,14S)-3-hydroxy-6-(methoxymethyl)-13-methyl-7,8,9,11,12,13,15,16-octahydro-6H-cyclopenta[a]phenanthren-17(14H)-one;
(6S,8R,9S,13S,14S)-6-(methoxymethyl)-13-methyl-7,8,9,11,12,13,14,15,16,17-decahydro-6H-cyclopenta[a]phenanthrene-3,17-diol;
(6R,8R,9S,13S,14S)-6-(methoxymethyl)-13-methyl-7,8,9,11,12,13,14,15,16,17-decahydro-6H-cyclopenta[a]phenanthrene-3,17-diol;
(6S,8R,9S,10R,13S,14S)-17-hydroxy-6-(methoxymethyl)-10,13-dimethyl-6,7,8,9,10,11,12,13,14,15,16,17-dodecahydro-3H-cyclopenta[a]phenanthren-3-one;
(6R,8R,9S,10R,13S,14S)-17-hydroxy-6-(methoxymethyl)-10,13-dimethyl-6,7,8,9,10,11,12,13,14,15,16,17-dodecahydro-3H-cyclopenta[a]phenanthren-3-one;
(6S,8R,9S,13S,14S)-6-(hydroxymethyl)-13-methyl-7,8,9,11,12,13,14,15,16,17-decahydro-6H-cyclopenta[a]phenanthrene-3,17-diol;
(6R,8R,9S,13S,14S)-6-(hydroxymethyl)-13-methyl-7,8,9,11,12,13,14,15,16,17-decahydro-6H-cyclopenta[a]phenanthrene-3,17-diol;
(6R,8R,9S,10R,13S,14S)-6-(methoxymethyl)-10,13-dimethylhexadecahydro-1H-cyclopenta[a]phenanthrene-3,17-diol;
(6R,8R,9S,13S,14S)-6-((aminooxy)methyl)-13-methyl-7,8,9,11,12,13,14,15,16,17-decahydro-6H-cyclopenta[a]phenanthrene-3,17-diol;
(6S,8R,9S,13S,14S)-6-((aminooxy)methyl)-13-methyl-7,8,9,11,12,13,14,15,16,17-decahydro-6H-cyclopenta[a]phenanthrene-3,17-diol;
(6R,8R,9S,13S,14S)-6-((aminooxy)methyl)-17-hydroxy-13-methyl-6,7,8,9,10,11,12,13,14,15,16,17-dodecahydro-3H-cyclopenta[a]phenanthren-3-one;
(6S,8R,9S,13S,14S)-6-((aminooxy)methyl)-17-hydroxy-13-methyl-6,7,8,9,10,11,12,13,14,15,16,17-dodecahydro-3H-cyclopenta[a]phenanthren-3-one;
(6R,8R,9S,13S,14S)-6-(((methoxymethyl)amino)methyl)-13-methyl-7,8,9,11,12,13,14,15,16,17-decahydro-6H-cyclopenta[a]phenanthrene-3,17-diol;
(6S,8R,9S,13S,14S)-6-(((methoxymethyl)amino)methyl)-13-methyl-7,8,9,11,12,13,14,15,16,17-decahydro-6H-cyclopenta[a]phenanthrene-3,17-diol;
1-((((6R,8R,9S,13S,14S)-3,17-dihydroxy-13-methyl-7,8,9,11,12,13,14,15,16,17-decahydro-6H-cyclopenta[a]phenanthren-6-yl)methyl)amino)propan-2-one;
1-((((6S,8R,9S,13S,14S)-3,17-dihydroxy-13-methyl-7,8,9,11,12,13,14,15,16,17-decahydro-6H-cyclopenta[a]phenanthren-6-yl)methyl)amino)propan-2-one;
(6R,8R,9S,13S,14S)-6-methoxy-13-methyl-7,8,9,11,12,13,14,15,16,17-decahydro-6H-cyclopenta[a]phenanthrene-3,17-diol;
(6S,8R,9S,13S,14S)-6-(2-methoxyethyl)-13-methyl-7,8,9,11,12,13,14,15,16,17-decahydro-6H-cyclopenta[a]phenanthrene-3,17-diol;
(6R,8R,9S,13S,14S)-6-(4-methoxybutyl)-13-methyl-7,8,9,11,12,13,14,15,16,17-decahydro-6H-cyclopenta[a]phenanthrene-3,17-diol;
(6R,8R,9S,13S,14S)-6-(6-methoxyhexyl)-13-methyl-7,8,9,11,12,13,14,15,16,17-decahydro-6H-cyclopenta[a]phenanthrene-3,17-diol;
(6R,8R,9S,13S,14S)-6-(6-methoxyoctyl)-13-methyl-7,9,11,12,13,14,15,16,17-decahydro-6H-cyclopenta[a]phenanthrene-3,17-diol;
(6R,8R,9S,13S,14S)-3-hydroxy-6-(methoxymethyl)-13-methyl-7,8,9,11,12,13,14,15,16,17-decahydro-6H-cyclopenta[a]phenanthren-17-yl stearate;
(6R,8R,9S,10R,13S,14S)-6-(methoxymethyl)-10,13-dimethyl-7,8,9,10,11,12,13,14,15,16-decahydro-3H-cyclopenta[a]phenanthrene-3,17(6H)-dione;
(6S,8R,9S,10R,13S,14S)-6-(methoxymethyl)-10,13-dimethyl-7,8,9,10,11,12,13,14,15,16-decahydro-3H-cyclopenta[a]phenanthrene-3,17(6H)-dione;
(6R,8R,9S,10R,13S,14S)-6-(methoxymethyl)-10,13-dimethyl-4,5,6,7,8,9,10,11,12,13,14,15,16,17-tetradecahydro-3H-cyclopenta[a]phenanthrene-3,17-diol;
(6S,8R,9S,10R,13S,14S)-6-(methoxymethyl)-10,13-dimethyl-4,5,6,7,8,9,10,11,12,13,14,15,16,17-tetradecahydro-3H-cyclopenta[a]phenanthrene-3,17-diol;
(6S,8R,9S,13S,14S)-6-(methoxymethyl)-13-methyl-17-oxo-7,8,9,11,12,13,14,15,16,17-decahydro-6H-cyclopenta[a]phenanthren-3-yl hydrogen sulfate;
(6R,8R,9S,13S,14S)-6-(methoxymethyl)-13-methyl-17-oxo-7,8,9,11,12,13,14,15,16,17-decahydro-6H-cyclopenta[a]phenanthren-3-yl hydrogen sulfate;
(6R,8R,9S,13S,14S)-13-methyl-6-(4-propoxybutyl)-7,8,9,11,12,13,14,15,16,17-decahydro-6H-cyclopenta[a]phenanthrene-3,17-diol;
(6R,8R,9S,13S,14S)-13-methyl-6-(5-ethoxypentyl)-7,8,9,11,12,13,14,15,16,17-decahydro-6H-cyclopenta[a]phenanthrene-3,17-diol;
(6R,8R,9S,10R,13S,14S)-6-(methoxymethyl)-10,13-dimethylhexadecahydro-1H-cyclopenta[a]phenanthrene-3,17-diol; and
(6R,8S,9S,14S,17S)-6-(methoxymethyl)-7,8,9,11,12,13,14,15,16,17-decahydro-6H-cyclopenta[a]phenanthrene-3,17-diol.

10. A method according to claim 9 wherein the compound is selected from the group consisting of
(6R,8R,9S,13S,14S)-6-(methoxymethyl)-13-methyl-7,8,9,11,12,13,14,15,16,17-decahydro-6H-cyclopenta[a]phenanthrene-3,17-diol and
(6R,8R,9S,13S,14S)-6-(6-methoxyhexyl)-13-methyl-7,8,9,11,12,13,14,15,16,17-decahydro-6H-cyclopenta[a]phenanthrene-3,17-diol.

11. A method according to claim 10 wherein the disorder is selected from the group consisting of multiple sclerosis, central pontine myelinolysis, experimental autoimmune encephalomyelitis, acute disseminated encephalomyelitis, transverse myelitis, progressive multifocal leukoencephalopathy; Alzheimer's Disease, subacute sclerosing panencephalitis, post-infectious encephalomyelitis, chronic inflammatory demyelinating polyneuropathy, progressive supernuclear palsy, multifocual motor neuropathy, Guillain-BarréSyndrome, progressive multifocal leucoencephalopathy, Devic's Disease, Balo's concentric sclerosis, Krabbe disease, Adrenoleukodystrophy (ALD), Pelizaeus-Merzbacher disease, Canavan disease, childhood ataxia with central hypomyelination, Alexander's disease, Cockayne syndrome, Van der Knapp syndrome, Zellweger syndrom and Refsum disease.

12. A method according to claim 11 wherein the disorder is multiple sclerosis.

13. A method according to claim 6 wherein monitoring the subject for remyelination is performed by an improvement of a symptom of a demyelinating disorder.

14. A method according to claim 13, wherein the compound is administered in combination with an anti-inflammatory or an immuno-modulator.

* * * * *